United States Patent
Gatica

(10) Patent No.: US 6,665,483 B2
(45) Date of Patent: Dec. 16, 2003

(54) APPARATUS AND METHOD FOR FILAMENT TENSIONING

(75) Inventor: Anthony William Gatica, Cedar Park, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 357 days.

(21) Appl. No.: 09/804,766

(22) Filed: Mar. 13, 2001

(65) Prior Publication Data

US 2002/0176680 A1 Nov. 28, 2002

(51) Int. Cl.$^7$ ................................................. G02B 6/00
(52) U.S. Cl. ....................... 385/136; 385/137; 385/147
(58) Field of Search ................................. 385/135, 136, 385/147, 137, 138; 81/9.51; 30/386

(56) References Cited

U.S. PATENT DOCUMENTS

| | | | |
|---|---|---|---|
| 4,410,561 A | 10/1983 | Hart, Jr. | 427/54 |
| 4,434,554 A | 3/1984 | Korbelak | 30/90.8 |
| 4,511,095 A | 4/1985 | Ideno et al. | 242/18 |
| 4,623,156 A | 11/1986 | Moisson et al. | 279/106 |
| 4,630,406 A | 12/1986 | Butler | 51/285 |
| 4,653,681 A | 3/1987 | Dreibelbis et al. | 228/4.5 |
| 4,662,307 A | 5/1987 | Amos et al. | 118/50.1 |
| 4,865,411 A | 9/1989 | Darsey et al. | 350/96.21 |
| 4,976,596 A | 12/1990 | Darsey et al. | 425/117 |
| 5,022,735 A | 6/1991 | Dahlgren | 350/96.21 |
| 5,114,066 A | 5/1992 | Amador et al. | 228/4.5 |
| 5,269,181 A * | 12/1993 | Gibson et al. | 73/160 |
| 5,269,206 A | 12/1993 | Yagawa | 81/9.51 |
| 5,340,371 A | 8/1994 | Dyott | 65/501 |
| 5,451,294 A | 9/1995 | Kolasinski et al. | 216/7 |
| 5,481,638 A | 1/1996 | Roll et al. | 385/134 |
| 5,684,910 A | 11/1997 | Chapin et al. | 395/128 |
| 5,894,540 A | 4/1999 | Drewing | 385/135 |
| 5,939,136 A | 8/1999 | Cronk et al. | 427/163.2 |
| 5,988,556 A | 11/1999 | Bednarczyk et al. | 242/476.2 |
| 6,027,062 A | 2/2000 | Bacon et al. | 242/474.7 |
| 6,069,988 A | 5/2000 | Kokura et al. | 385/37 |
| 6,088,503 A | 7/2000 | Chandler et al. | 385/135 |
| 6,123,801 A | 9/2000 | Miller | 156/344 |
| 6,129,951 A * | 10/2000 | Ward-Close et al. | 427/255.24 |

FOREIGN PATENT DOCUMENTS

| | | | |
|---|---|---|---|
| JP | 60-122754 | 7/1985 | C03C/25/02 |
| JP | 61-40846 | 2/1986 | C09C/25/02 |
| JP | 09 280998 | 10/1997 | |
| WO | WO 00/02075 | 1/2000 | |

OTHER PUBLICATIONS

International Search Report for PCT/US01/20373.
Method for recoating optical fibres with polyimide–Electronics Letters Jun. 11, 1998 Vo. 34. No. 12.
09/805,473–55861USA5A–Claims for Filament Recoating Apparatus and Method.
09/804,760–55862USA3A–Claims for Filament Recoating Apparatus and Method.
09/804,787–55891USA2A Claims for Filament Organizer.
09/804,847–55894USA6A–Claims for Apparatus and Method for Removing Coatings From Filaments.
09/804,767–56436USA5A–Claims for Refractive Index Grating Manufacturing Process.
09/804,761–56437USA3A–Claims for Chemical Stripping Apparatus and Method.
09/804,757–56438USA1A–Claims for Force Equalizing Filament Clamp.

* cited by examiner

Primary Examiner—Chandrika Prasad
(74) Attorney, Agent, or Firm—Alan Ball; Gregg Rosenblatt

(57) ABSTRACT

A method and article for applying tension to a filament using a filament tensioning apparatus comprising a tensioning holder including at least one support bar. A first carriage is mounted at a first location on a support bar. The first carriage has a first clamp and a voice coil mounted thereon for movement relative to a support bar. A second carriage mounted at a second location on a support bar provides a separation between the first location and the second location. The second carriage has a second clamp and a load cell mounted thereon for movement relative to a support bar. A guide bar extends from the voice coil for contact with the load cell to adjust the separation of the first location from the second location to apply tension to a filament held between the first clamp and the second clamp.

13 Claims, 15 Drawing Sheets

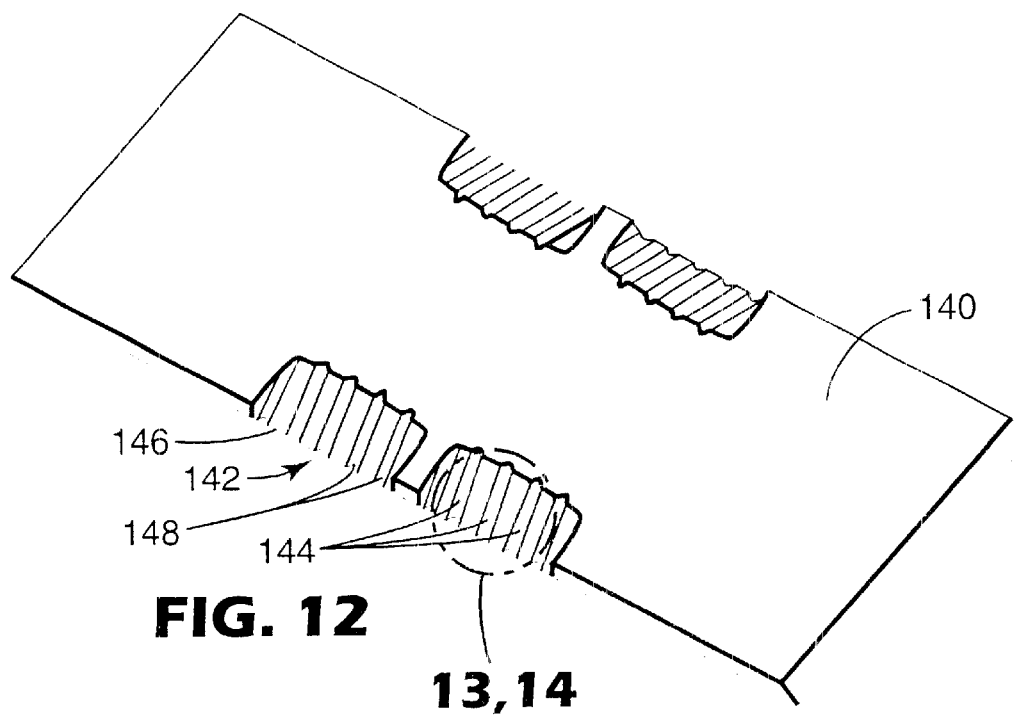
FIG. 12
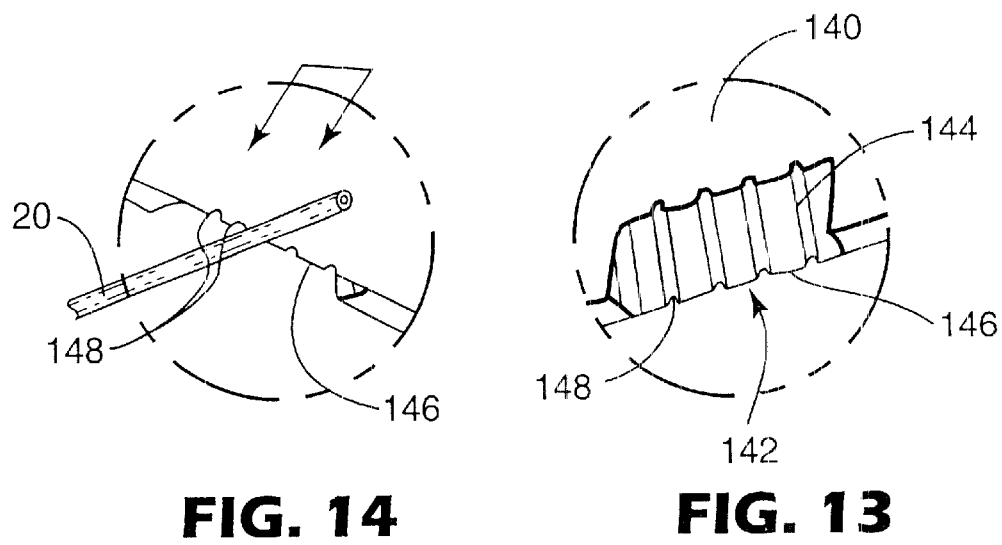
FIG. 14  FIG. 13

APPARATUS AND METHOD FOR FILAMENT TENSIONING

FIELD OF THE INVENTION

The invention relates to a process and equipment for conveniently handling a filament in the form of an optical fiber during multiple processing operations that may be at least partially automated. More particularly the invention relates to compact handling of optical fibers during manufacturing operations to include Bragg gratings in at least a portion of their length via a series of manufacturing operations including mechanical stripping, acid stripping, Bragg grating writing, and optical fiber recoating and testing.

BACKGROUND OF THE INVENTION

Glass has been used for centuries as a material of choice in a variety of scientific and domestic applications. From the early use of prismatic glass for separating light into its component colors, glass has been widely used in optical devices that control or adjust the properties of light beams. A recent and rapidly expanding application of the light modifying properties of glass structures involves the drawing of fine filaments of highly purified glass, more commonly referred to as optical fibers, that direct light signals between light transmitting and receiving locations During the late 1970s utilities began using optical fiber installations for internal communication, and by the early 1980s, a number of small optical fiber networks were installed. The use of such networks has been growing ever since to replace existing coaxial cable systems. Advantages provided by optical fiber communications networks include lower cost, the use of fewer signal repeaters to correct for signal distortion, and a higher signal carrying capacity than coaxial cable networks.

The capacity of fiber optic systems continues to increase. In 1980, the first systems could transmit 45 megabits per second. Current systems transmit up to 5 gigabits per second. So extensive is the modern use of optical fiber networks that fiber optic networks have essentially replaced all transcontinental copper cable networks and entirely new networks are being created continually. One prediction claims that every continent in the World will become part of a global fiber optic network.

A fiber optic system includes three main parts of transmit circuitry and light source, light detector and receiver circuitry, and fiber. The transmit circuitry converts electronic signals to modulate a light source that generates light signals for transmission. Connection from the light source to a length of optical fiber facilitates transmission of light signals for distances covered by the optical fiber. Attachment of light detector and receiver circuitry at the terminal end of a fiber produces a communication link The use of multiple communication links provides extended networks of transmitters and receivers.

Interconnection of fiber optic networks requires high precision devices in the form of optical connectors that join optical fibers to peripheral equipment and other optical fibers while maintaining adequate signal strength. In operation an optical connector centers the small fiber so that the light gathering core lies directly over and in alignment with a light transmitting source or another fiber. Sections of optical fiber may also be spliced together using mechanical splicing or fusion splicing techniques.

Special features may be built into selected, relatively short lengths of optical fibers to be spliced into fiber optic networks. A fiber Bragg grating represents a light-modifying feature that may be introduced or written into an optical fiber by simple exposure to ultraviolet light. The ability to write such gratings leads to a variety of devices. For example, Bragg gratings may be applied in telecommunications systems to control the wavelength of laser light, to introduce dispersion compensation, and, in the form of long period gratings, to modify the gain of optical fiber amplifiers. Fiber optic applications of fiber Bragg gratings, outside of telecommunications, include spectroscopy and remote sensing.

The process of introducing special features such as Bragg gratings into an optical fiber may include a number of steps requiring handling of relatively short lengths of optical fiber during a series of manufacturing operations. An optical fiber typically requires removal of protective coatings before changing the physical characteristics of the fiber to include a Bragg grating. After writing a Bragg grating, the fiber may be annealed and recoated.

Little has been revealed about the automation of processes to alter the characteristics of a fiber to provide it with a refractive index grating. Some evidence exists of individual processing steps but not of a type that may be readily incorporated in an automated sequence. Fiber loading for example is described in U.S. Pat. No. 5,988,556. This patent refers to automated winding of a continuous length of fiber from a fiber supply onto first and second sections of a shipping spool. The winder comprises a first device that collects a first portion of a continuous length of fiber and winds it onto the first section of the spool, and a second device for winding a second portion of the continuous fiber onto the second section of the spool. There is no evidence to show that the spooled fiber has a use other than as a shipping package. U.S. Pat. No. 6,027,062 describes an automated winder including fiber supply and collecting devices that move a fiber to a threading device that automatically threads the fiber onto a spool. This is similar to the goal of U.S. Pat. No. 4,511,095 to form of a coil of fiber wound onto a bobbin or similar structure.

The use of stackable cassettes for handling and organizing optical fibers is well known, particularly for storage of lengths of spliced fibers. Cassettes typically comprise shallow dish-shaped holders and enclosures for containment of loosely coiled optical fibers. Loose optical fiber coils do not have the same compact structure as spooled optical fibers. An intermediate form of coiled fiber, described in U.S. Pat. No. 5,894,540, may be produced using an assembly for holding a length of filamentary material in a wrapped configuration with a minimum bend radius. The filament or fiber may be wrapped around spools attached to a support plate. Adjustment of the spacing between spools removes slack from the fiber wrapped around them. Fiber cassettes and related fiber holding assemblies place loose fiber in a tidy condition for storage, usually following interconnection of lengths of optical fiber. U.S. Pat. No. 6,088,503 confirms the use of optical fiber cassettes as holders of optical fibers before, during and after splicing. The patent describes a clamping tool designed to align and hold a pair of fiber ends in preparation for optical fiber splicing.

Cassettes and related fiber organizing assemblies provide tidy storage for optical fibers around connected and spliced sections of optical fiber. There appears to be no evidence of such storage containers used for processing organized lengths of optical fiber during the manufacture of optical fiber devices. One manufacturing process requires the removal of protective buffers and coatings to reveal the bare surface of an optical fiber. Several processes are known for removing protective layers, such as buffers and coatings, from the surface of optical fibers. They include mechanical stripping, chemical stripping and thermal stripping.

Mechanical stripping of optical fibers and related coated filaments requires careful positioning of sharp tempered metal blades to expose a bare surface portion of a fiber without cutting or scratching or otherwise physically damaging the fiber surface. Known methods of mechanical stripping relate to cutting blade design and how a coating may be removed from the surface of a fiber. The predominant use of mechanical stripping involves the removal of protective layers from the ends of optical fibers, insulated wires and related filaments, prior to joining the filament ends together. U.S. Pat. No. 4,434,554 describes an optical fiber stripping device including a flat base having a number of fiber receiving channels of suitable depth to ensure only removal of a buffer coating from each fiber, when a blade penetrates the coating. The blade moves parallel to the axis of a fiber or group of fibers using a paring action to remove protective material. Channel size, based upon fiber diameter determines the selection of a flat base to provide a device that strips a fiber end without damaging the fiber itself.

One way to avoid damage to the bare surface of an optical fiber requires the use of blades designed to penetrate the protective buffer or fiber coating without reaching the fiber surface. Suitable blades have a substantially semicircular sharpened edge of a radius slightly larger than the radius of the bare optical fiber. Two opposing blades, penetrating the protective layer around the fiber, interfere with each other before the cutting edges reach the fiber surface. After penetrating a protective layer, close to the end of a fiber, movement of the blades parallel to the fiber axis displaces a section of the layer to provide a bare fiber end untouched by the blades. United States Patents, including U.S. Pat. Nos. 4,630,406, 5,269,206, 5,481,638, and 5,684,910, describe the manufacture and design of blades for cutting insulation from e.g. insulated electrical wires and optical fibers. Successful mechanical stripping using such blades may require additional treatments, including softening the protective layer as in U.S. Pat. No. 5,481,638 requiring a chemical filled chamber first to soften an encapsulating layer then to clean plastic material from the blades after stripping. U.S. Pat. No. 5,684,910 teaches an optical fiber having improved mechanical strippability. The improvement includes the use of a frangible boundary layer between a fiber coating and a buffer to facilitate separation from the bare fiber. Previous teachings include initial blade movement perpendicular to a filament axis, to penetrate a coating, followed by movement parallel to the filament axis to expose bare filament ends by displacement of protective layers.

Chemical stripping may be used as an alternative to mechanical stripping for preparing bare fiber ends. United States Patents, U.S. Pat. Nos. 4,865,411 and 4,976,596 deal with controlled removal of coating, by gradual withdrawal of a coated fiber from a chemical bath, to produce a contoured shallow taper adjacent to the bare glass fiber surface. A fixture, according to U.S. Pat. No. 5,451,294 provides support while dipping the end of a coated optical fiber into a chemical bath to dissolve coating from the end. Chemical stripping methods include common problems related to the handling of chemicals especially, as in this case, when the chemical strippers involve corrosive liquids.

Hot gas stripping may be used instead of mechanical or chemical stripping. One example of this process, described in U.S. Pat. No. 6,123,801, uses a hot inert gas to melt buffer coating and blow it from the surface of an optical fiber. The process requires high pressure gas streams and temperatures in the region of 800° C. to strip coating from the fiber. U.S. Pat. No. 5,939,136 describes a process for preparing optical fiber devices including thermal removal of a coating from an optical fiber, preferably performed using a heated gaseous stream.

A reason for removing protective buffers and related coatings from optical fibers is the need to change the characteristics of the fiber such as by writing of a refractive index grating, also known as a Bragg grating, in the core of an optical fiber. Refractive index changes occur during exposure of a bare fiber to radiation from an ultraviolet laser or similar exposure device. The majority of protective coatings for optical fibers absorb the fiber modifying radiation. This explains the need to remove the coatings before writing a refractive index grating.

Without further processing, an optical fiber including a refractive index grating also has a bare portion that requires application of protective coatings before use in an optical fiber device. The widely accepted method for recoating bare sections of optical fibers involves special coating molds. Methods similar to those used to coat drawn fibers, during their manufacture have also been described.

A recoating mold, described in U.S. Pat. No. 4,410,561, provides a coated optical fiber using a split mold die structure. The size and design of a cavity formed by the closed mold provides space that becomes filled during injection of curable, protective, fluid recoating compositions. It is desirable to avoid entrapment of air inside the mold since this could lead to a defective recoated fiber section. Complete filling of a mold cavity may involve intentional application of pressure. U.S. Pat. No. 5,022,735 uses a screw type plunger to pressurize recoating fluid injected into a conventional recoating mold. Some recoating molds include curing means to provide finished recoated sections of optical fibers. U.S. Pat. No. 4,662,307, for example, uses a split mold including an injection port and UV light port through which light passes to cure recoating compositions. The curing process requires multiple light sources.

Application of coatings to an optical fiber drawn from a pre-form typically places the emerging fiber in a vertical orientation. As it travels downward, the fiber may pass through a reservoir of coating fluid before exiting through an orifice sized to the desired external diameter of the coated fiber. It is possible to apply such a process to recoating of bare sections of optical fiber including a Bragg grating, as taught in U.S. Pat. No. 6,069,988. Upon exit from the orifice, the fiber moves past a source of curing radiation. The curing radiation differs from the radiation used for writing the Bragg grating so as not to destroy or change the characteristics of the grating.

There is evidence in Japanese Patents JP 60-122754 and JP 61-40846 for spraying protective plastic coatings on optical fibers exiting a draw tower. Coverage of the full circumference of the optical fiber requires the uses of either multiple spray heads or special spray containment shrouds. The use of multiple spray heads deposits only a fraction of the spray on the surface of the drawn fiber while the use of special shrouds involves complicated threading of a fiber.

Each point in the processes, of fiber stripping, modifying and recoating, requires care to prevent damaging the fragile optical fiber. Damage to optical fibers may occur by physical contact or exposure to tensile, torsional, twisting, and bending stresses. Excessive bending can change the optical characteristics of a fiber. Failure to meet required optical characteristics leads to rejection of an optical device and increases the expense of device manufacture. A need exists for improved means for handling optical fibers for post draw processing, to reduce incidence of damage thereby reducing the cost and increasing the yield of optical fiber devices.

SUMMARY OF THE INVENTION

The present invention satisfies the need for effective and compact handling of filamentary materials during manufacturing operations including process steps that produce structural and related changes in the filament. When applied to optical fibers, an article, also described herein as a filament organizer, provides compact containment of an optical fiber. The filament organizer allows relatively precise positioning of at least a portion of an optical fiber to facilitate processing of optical fibers related to optical couplers, fused couplers and tapered fiber devices and the like. Optical fiber modification may also refer to actions taken to change the inherent characteristics of an optical fiber or to incorporate an optical fiber into a functional assembly. The inherent characteristics of an optical fiber change with adjustment of its refractive index properties, as in the formation of a variety of fiber Bragg gratings. Incorporation of an optical fiber into a functional assembly provides useful devices such as temperature compensated fiber Bragg gratings. Refractive index changes and functional assembly production, according to the present invention, use a filament organizer that distributes an optical fiber between a lockable spool and a rotary spool to expose a central portion of a fiber to be modified.

A computer controlled, or otherwise programmed, fiber dispenser may be used to load a prescribed amount of a substantially twist-free optical fiber between a pair of spools mounted on a common axis. After fiber loading the spools are separated, with fiber extending between them, and mounted to a filament organizer for fiber storage and further processing. Use of computer controlled dispensing, combined with a filament organizer, allows accurate consistent loading and organization of a selected length of optical fiber within the boundaries of the filament organizer. Control of the loading process allows the production of numerous holders containing approximately equal lengths of fiber, organized in similar fashion. After successful loading of an optical fiber, a filament organizer provides a convenient article for handling the fiber through process operations required for the manufacture of optical fiber devices. Preferably the filament organizer includes means for applying a tension force between about 50 g to about 100 g to the filament held therein.

A variety of devices use optical fibers that have been structurally modified to include in-line optical waveguide refractive index gratings in at least a portion of their length. Physical property variation of gratings allows them to be tailored for specific applications. In one embodiment, the present invention provides a fiber Bragg grating obtained via a series of manufacturing operations including mechanical stripping of an optical fiber, acid stripping, pigtailing, optical fiber Bragg grating writing, annealing and optical measurement followed by recoating and testing. The final step of testing, including fiber proof testing, confirms attainment of performance requirements desired of an optical fiber Bragg grating.

Each operation or step of the manufacturing process requires attachment of one or more filament organizers to one or more filament processors or apparatus designed specifically to accomplish a designated step. This requires that the size and shape of a filament organizer include aspects of design allowing convenient connection with several filament processors. As well as making suitable connection with several types of filament processors, an important requirement of a filament organizer is containment of a prescribed length of filament that may be up to several meters in length. Preferably, in the case of an optical fiber, a filament organizer holds most of the length of a filament on a pair of spools leaving a portion of filament available for processing. A spool holds two sections of optical fiber wound in the same direction on separate sides of a divided spool core. One section of fiber extends between a pair of spools while the other section of optical fiber provides a pigtail portion that may be readily unwound from each spool. There is a pigtail section at each end of a continuous length of optical fiber.

After winding a continuous length of optical fiber between a pair of spools and positioning the spools on a support board, fiber handling may proceed with reduced expectation of damage to the fiber. Also the use of a filament organizer allows ready access to a portion of fiber. Ready access to this portion of fiber allows it to be modified initially by removal of protective coatings from its surface and thereafter subjecting it to operations that change its physical and optical properties, as in the writing of a fiber Bragg grating into a bared portion of optical fiber. A filament organizer allows reproducible positioning of that portion of an optical fiber that will be modified. Reproducible positioning leads to predictable results of filament or optical fiber modification by operations that may be conducted using a process where at least several of the steps may be automated.

As indicated previously, a filament organizer provides a portion of filament or optical fiber suitably positioned for processing. Formation of an optical fiber Bragg grating according to the present invention requires that any polymeric protective coating, also referred to herein as a buffer coating, should be removed prior to the writing of the fiber Bragg grating. The coating may be removed using liquid or mechanical or thermal stripping.

An optical fiber covered with a single polymeric layer, referred to herein as a primary buffer, may require only liquid stripping using concentrated acid to remove the buffer. Removal of multiple protective coatings, including primary and secondary buffers according to the present invention, preferably uses a combination of mechanical stripping followed by acid stripping. Acid stripping herein refers to dissolving residual coating material in an acid medium with displacement of the acid using a water rinse and solvent wash applied to at least a portion of the fiber. Initial displacement of coating requires specially designed mechanical stripping equipment that cooperates with a filament organizer for precise positioning of the portion of an optical fiber from which protective coating will be displaced. Mechanical stripping equipment may be designed for conveniently processing one filament organizer or several combined in a single stacked configuration. This results in treatment of one or more fibers at a time depending on the number of filament organizers. Coating displacement, via mechanical stripping, creates gaps to the bare fiber through which acid may subsequently penetrate to more rapidly dissolve coating from the fiber portion.

Removal of coating by acid stripping preferably requires an apparatus that forms a loop of filament for each filament organizer included in a stacked configuration. The apparatus is constructed for formation of individual filament organizer loops having approximately the same size. The plane of each loop parallels that of its nearest neighbors. Acid stripping of one or more fiber loops occurs by immersing the arcuate portion of a loop into an acid bath. The depth of immersion of each loop into the acid bath controls the length of protective coating removed from a fiber to provide an optical fiber having a bare portion stripped to the silica surface of the fiber. Acid stripping provides a bare fiber surface that is substantially free from contaminants.

After all of the fibers in a stacked configuration have been mechanically stripped and acid stripped, the pigtail ends of each fiber are manually unwound and organized into groups using pigtail connectors. Pigtail ends trail about one meter from each end of a filament organizer.

As a further refinement, a filament organizer according to the present invention may include a conventional optical fiber connector for terminating optical fiber ends on the surface, and within the boundaries of the filament organizer. Optical connector termination of fibers reduces the length of pigtail portions of an optical fiber while still providing convenient points of attachment to external optical fiber devices. Compact fiber organization of this type distributes the length of an optical fiber on the surface of a filament organizer without any part of the fiber hanging over the edges of the organizer. Any of a variety of optical fiber device interconnects may be used to reduce the overall length of an optical fiber by shortening the pigtail ends. Reduction in the overall length of an optical fiber translates into cost savings associated with each filament organizer equipped with pigtail to optical fiber connector termination.

Following organization by grouping of pigtail ends each filament organizer in a stacked configuration provides a clean, dry, bare fiber portion ready for positioning in a fiber Bragg grating writing apparatus. After release of tension from a filament held by a filament organizer, the Bragg grating writing apparatus applies a selected tension to the portion of an optical fiber before it is modified to produce a Bragg grating. Production of multiple optical fiber Bragg gratings, having a substantially identical wavelength response, requires precise alignment and application of the same amount of tension to each optical fiber portion loaded into the fiber Bragg grating writing apparatus. Precise alignment of an optical fiber portion with the Bragg grating writing apparatus relies on features built into a filament organizer and the grating writing apparatus respectively for consistent relative positioning of one to the other. Consistent loading and fiber portion tensioning relies upon the use of a voice coil drive mechanism and air suspended bearings that facilitate accurate fine adjustment essentially free from drag.

After placing an appropriate portion of an optical fiber under tension in the fiber Bragg grating writing apparatus, the progress of Bragg grating writing may be monitored by observing a display of the wavelength envelope produced by the writing process. Signal information proceeds from an optical fiber to suitable monitoring equipment through connections between the equipment and pigtail ends of a fiber. This provides feedback of the quality of a grating at the time of writing and represents a convenient decision point for acceptance or rejection a fiber Bragg grating as it is written.

Annealing of fibers takes place in a thermal annealing apparatus and fulfils several requirements upon completion of writing of fiber Bragg gratings. This step of the process proceeds at a temperature of approximately 300° C. for a duration of more than about three minutes. The annealing process stabilizes the Bragg grating against wavelength drift for time periods exceeding about twenty to about twenty-five years.

After annealing and optical confirmation that the grating center wavelength meets requirements, the fibers and associated Bragg gratings are ready for recoating before final testing. The recoating operation uses equipment designed for a filament organizer or preferably a stacked configuration of filament organizers according to the present invention. It is possible to use in-mold recoating, spray recoating or an extrusion die coating process to recoat the previously stripped portion of each optical fiber. Injection die coating refers herein to conventional in-mold die recoating. Spray recoating uses multiple passes of an optical fiber between a spray head and a radiation curing source. The extrusion recoating process uses a split die that may be positioned around an optical fiber for application of a curable coating composition around the circumference of the fiber as the extrusion head traverses the length of an uncoated fiber portion. Preferably the die head includes a radiation source and the extruded coating cures by exposure to the radiation source. This allows application of recoating material followed immediately by curing.

Application of recoating material to protect a Bragg grating formed in an optical fiber represents the final processing operation for producing fiber Bragg gratings that may be used in telecommunications and related applications. A final check of the resulting product determines if it passes tensile strength and visual inspection requirements. After successfully meeting requirements, the spools holding a finished optical fiber Bragg grating may be detached from the filament organizer and used for conveniently holding, packaging and transporting the final product. A convenient form of packaging for transportation requires transfer of the full continuous length of a fiber Bragg grating to one spool after removing it from the filament organizer. The design of a spool provides a protective cover for the fiber Bragg grating element following transfer of the full length of optical fiber to one spool.

More particularly, the present invention provides a method for manufacturing an optical fiber refractive index grating. A suitable method comprises the steps of providing a substantially twist-free length of an optical fiber between a first spool and a second spool, for attachment of the first spool and the second spool to a support. The support has a first surface opposite a second surface, to provide a filament organizer including the first spool as a lockable spool and the second spool as a rotary spool. The filament organizer further comprises a tensioner coupled to the rotary spool to apply tension to at least a central portion of the length of an optical fiber disposed between the lockable spool and the rotary spool. Further processing of a fiber under tension includes removing at least a buffer coating from the central portion of an optical fiber before applying a controlled tension to the central portion of an optical fiber. A refractive index grating may then be written by changing the refractive index characteristics of the central portion during exposure of the central portion to an interference pattern of high intensity actinic radiation, to produce the refractive index grating. After formation the grating may be annealed and the resulting fiber device proof tested to confirm desired performance properties.

The method described previously uses a filament organizer, comprising a support having a first surface opposite a second surface and further including organizing mounts joined to said first surface and spacer blocks attached to said second surface. The filament organizer has a lockable spool adjacent to the first surface of the support, a rotary spool adjacent the first surface of the support, and a tensioner attached to the second surface of the support. The tensioner includes a tension wire for attachment to the rotary spool to apply tension thereto to transmit tension to a filament disposed between the lockable spool and the rotary spool. A tension relief assembly allows selective reduction of tension applied to a filament. The tension relief assembly includes the tension wire, providing connection between the tensioner and the rotary spool, a tension wire access, and at least one pulley for aligning the tension wire with the tension wire access. Other parts of the filament organizer include at least one mounting plate integrally formed with the support and extending outwardly therefrom, and at least one guide defining a filament path between the lockable spool and the rotary spool. Further the guide is rotationally mounted on the mounting plate, adjacent to the first surface of the support, to provide spacing of the filament path from the support.

During refractive index grating manufacture a mechanical stripping apparatus displaces resin from a resin covered filament, in the form of an optical fiber, by forming a removable sleeve portion between opposing filament ends. The mechanical stripping apparatus comprises a base that has a first clamp attached to the base to hold a filament at a first location. A second clamp is attached to the base and has a separation from the first clamp and is in axial alignment therewith for holding a filament at a second location. The apparatus includes a first set of cutting blades mounted on the base adjacent to the first clamp. The first set of cutting blades includes a first upper blade and a first lower blade. Each of the upper and lower blades includes an arcuate sharpened edge for cutting into resin around a resin covered filament proximate to the first location. A second set of cutting blades is mounted on the base adjacent to the second clamp such that a distance separates the first set of cutting blades from the second set of cutting blades. The distance between cutting blades is less than the separation between the clamps. The second set of cutting blades includes a second upper blade and a second lower blade with each blade including an arcuate knife edge for cutting into resin around a resin covered filament proximate to the second location. A blade actuator secured to the base, and coupled to the first set of cutting blades and the second set of cutting blades, moves the first upper blade and the first lower blade together. During this movement the sharpened edges penetrate resin around a resin covered filament proximate to the first location. The blade actuator also moves the second upper blade and the second lower blade together for the knife edges to penetrate resin around a resin covered filament proximate to the second location. A biasing component also on the base moves the first set of cutting blades and the second set of cutting blades towards each other during displacement of resin from a resin covered filament to form the removable sleeve portion.

The removable sleeve portion may be formed using a method for displacing resin from a resin covered optical fiber between opposing fiber ends. The method provides a mechanical stripping apparatus comprising a first clamp for holding an optical fiber at a first location, a second clamp having a separation from the first clamp and in axial alignment therewith for holding an optical fiber at a second location. A first set of cutting blades, of the mechanical stripping apparatus, is adjacent to the first clamp for cutting into resin around a resin covered optical fiber proximate to the first location. A second set of cutting blades is adjacent to the second clamp for cutting into resin around a resin covered optical fiber proximate to the second location. A distance separates the first set of cutting blades from the second set of cutting blades. The distance is less than the separation between the first and second clamps. The first set of cutting blades and the second set of cutting blades are adapted for movement towards each other during removal of resin from a resin covered optical fiber to form the removable sleeve portion. Resin displacement further includes clamping an optical fiber in the first clamp and clamping the optical fiber in the second clamp such that the optical fiber is under tension. Operating the first set of cutting blades and the second set of cutting blades, for cutting into the resin, produces the removable sleeve that has a gap at each end thereof. The gap at each end exposes a bare filament portion separating the removable sleeve portion from a tapered transition formed in the resin during cutting of the resin as the first and second set of cutting blades move towards each other.

In another aspect according to the present invention an apparatus may be used to form a loop in a section of a filament prior to chemical stripping of resin from e.g. an optical fiber. The apparatus comprises a container including a front wall having a front guide slot formed therein and a rear wall having a rear guide slot formed therein coplanar and parallel to the front guide slot. The container further includes a floor containing at least one slit formed between and parallel to the front wall and the rear wall. A first filament gripper includes a stationary elastomer roller and a positionable cylinder holding a filament therebetween, at a first location thereof. The stationary elastomer roller is rotatably mounted from the front wall to the rear wall, so that the positionable cylinder is mounted, adjacent to the stationary elastomer roller, between the front guide slot and the rear guide slot for repositioning therein. A second filament gripper includes a movable elastomer roller and a movable cylinder holding the filament therebetween, at a second location. The second filament gripper has a separation from the first filament gripper and has substantially axial alignment therewith. The second filament gripper moves towards the first filament gripper to reduce the separation to bring the first location closer to the second location thereby producing a loop of filament between the first filament gripper and the second filament gripper. The loop of filament extends through a slit to below said floor of the container where it may be introduced into a reservoir having a solvent therein to surround at least a portion of the loop of filament to dissolve resin from the portion of the loop. A loop forming container according to the present invention may be sized to accommodate one or more filament organizers having a filament between a lockable spool and a rotary spool. Steps for forming one or more filament loops using a loop forming container may be included in a process for chemically stripping resin from a resin coated filament, preferably as an optical fiber.

Processing of a filament according to the present invention requires the use of a filament holding fixture comprising a gripper having an open position and a closed position. The gripper further comprises a lower jaw mount, and a lower jaw connected to the lower jaw mount, the lower jaw having a planar surface and an open-ended, V-shaped channel formed therein opening to the planar surface to receive at least a portion of a filament. The filament holding fixture also has an upper jaw mount, and an upper jaw assembly. The upper jaw assembly comprises a support flange attached to the upper jaw mount. The support flange includes a support surface, having a substantially conical recessed portion. A fiber clasp, included in the upper jaw assembly, has a contact face opposite a structured surface. The structured surface includes an open-ended groove of substantially rectangular cross section. There is a substantially conical depressed portion formed in the contact face of the fiber clasp. The open ended groove and the V-shaped channel are in longitudinal alignment to contact at least a portion of a filament when the gripper is in the closed position. A plurality of spring connectors hold the fiber clasp to the support flange. Also, an angular compensator is confined between the recessed portion of the support surface and the depressed portion of the contact face by force produced by the plurality of spring connectors. The angular compensator maintains separation of the support flange from the fiber clasp to allow them to move independently. This leads to fine adjustment of the fiber clasp for applying substantially equal force at points of contact of the open-ended groove and the V-shaped channel with a filament, preferably an optical fiber, held therebetween following movement of the gripper from the open to the closed position.

The present invention further provides a filament tensioning apparatus for releasably securing a filament under tension. The tensioning apparatus comprises a tensioning holder and a pair of grippers. The tensioning holder includes at least one support bar, and a first carriage movably mounted at a first location on a support bar. The first carriage includes an upper surface having a first clamp and a voice coil mounted thereon for movement relative to a support bar. A second carriage is movably mounted at a second location on a support bar such that a separation exists between the first location and the second location. The second carriage includes an upper face having a second clamp and a load cell mounted thereon for movement relative to a support bar. The second clamp is in axial alignment with the first clamp to secure a measured filament portion including a bare portion thereof, located inside a first boundary and a second boundary, between the first clamp and the second clamp. A guide bar extends from the voice coil for contact with the load cell to adjust the separation of the first location from the second location, to change tension applied to the measured filament portion, during activation of the voice coil. The pair of grippers of the tensioning apparatus is in axial alignment with the fist clamp and the second clamp, to substantially immobilize the bare portion of the measured filament portion. A filament tensioning apparatus according to the present invention may include a coupling for attaching a filament organizer to position a filament, preferably an optical fiber, to be held between the first clamp and the second clamp. The filament organizer holds a filament between a lockable spool and a rotary spool.

A resin covered filament having had resin removed therefrom may require coating by a method that uses a filament recoating apparatus according to the present invention. Such a filament recoating apparatus comprises a frame for releasably securing a filament and a carriage mounted on the frame to oscillate between a first position and a second position. The recoating apparatus has a first filament holding fixture mounted on the carriage. A second filament holding fixture is also mounted on the carriage in axial alignment with the first filament holding fixture. The fixtures secure a measured filament portion including a bare portion thereof, located inside a first boundary and a second boundary, between the first filament holding fixture and the second filament holding fixture. At least one spray head is attached to the frame at the first position. A radiation source is attached to the frame at the second position. The measured filament portion moves between the spray head and the radiation source, during oscillation of the carriage between the first position and the second position to place the bare portion to receive a curable coating from the spray head. The spray head applies curable coating from the first boundary to the second boundary. Curing of the curable coating occurs by exposure to radiation from the radiation source. Droplets of curable coating composition may be deflected using a deflector, such as an air-knife, to selectively direct coating composition towards a plurality of bare filament portions of filaments, preferably optical fibers, grouped around a spray head. Different coating compositions may be applied to bare filament portions to provide recoated filaments using a first composition and overcoated filaments by application of a second coating composition over the first coating composition. The resulting filaments include a multilayer coating.

An alternative filament recoating apparatus, according to the present invention, comprises a planar surface and an extrusion coating assembly attached to the planar surface. The extrusion coating assembly comprises a first filament holding clamp and a second filament holding clamp opposite the first filament holding clamp. A measured filament portion including a bare portion thereof, located inside a first boundary and a second boundary, lies between the first filament holding clamp and the second filament holding clamp. A coating head, includes a die plate having formed therein an open ended channel including a wall having a fluid entry and a gas port formed therein adjacent a radiation source. The coating head further includes a cover die plate having formed therein an open ended elongate slot. The cover die plate has a hinged connection to the die plate for rotation of the cover die plate between an open position and a closed position. In the closed position the cover die plate lies adjacent to the die plate and the channel aligns with the elongate slot to form a tubular opening through the coating head to encircle a section of the bare portion. A linear transport mechanism adjacent to the coating head includes a guide rod and a carriage slidably mounted thereon for movement along the guide rod. A connecting rod from the carriage to the coating head provides linear displacement of the coating head during movement of the carriage to move the coating head from the first boundary to the second boundary. Curable fluid may be extruded from the fluid entry while energy from the radiation source cures the curable fluid to recoat the bare portion of a filament.

A method for extrusion coating a filament comprises the steps of providing a filament organizer having an extended filament between a fixed spool and a rotary spool to provide a measured filament portion and a bare filament portion of a filament, preferably an optical fiber. Recoating of the bare portion of a fiber follows attachment of the filament organizer to an extrusion coating fixture comprising a guide rod, a carriage movably mounted on the guide rod. A coating die, including a coating head and a radiation source, is joined to the carriage. The coating head has an opening for directing a curable coating composition to the bare filament portion positioned in a channel formed in the coating die and extending therethrough. A curable coating composition is applied to the bare filament portion to provide a recoated filament portion, followed by exposing the recoated filament portion to the radiation source for radiation curing of the curable coating composition applied to the bare portion.

Definitions

The terms "bare fiber," or "bare fiber portion," or "stripped fiber," or phrases relating to such terms refer herein to the portion of an optical fiber from which protective coating has been removed to expose the silica surface of the fiber.

As used herein, the term "cladding" refers to the outer layer of an optical fiber, as drawn.

The term "buffer" or "primary buffer" refers herein to a polymer or resin layer next to a bare fiber.

A "coating" or "secondary buffer" is used herein to describe a polymer or resin layer next to a buffer or primary buffer.

The term "resin" as used herein is a general term describing polymer coverings for filaments particularly optical fibers. Materials used for previously defined buffers and coatings fall within the general term of resin.

The term "filament" herein refers to a fiber structure, preferably a "silica filament." An optical fiber is a preferred form of filament according to the present invention.

A "tapered transition" describes the preferably graduated conical shape of the portion of buffer layers closest to a bare fiber portion after subjecting a coated optical fiber to mechanical stripping according to the present invention.

The term "ribbonizing" refers to the formation of a single layer of optical fibers, side by side, as a flat ribbon-like structure that facilitates the joining of ends of multiple fibers for insertion in one end of a fiber optic ribbon connector.

The term "angular compensator" or "ball joint leveler" as used herein means a self adjusting coupling inserted between parts of at least one jaw of a gripper to achieve optimum positional relationship between the contacting surface of the jaw and an object to apply even pressure over the surface of the object.

The use of a "non-contact" method for recoating bare portions of optical fibers means that no portion of the fiber touches any part of the recoating equipment. This is a benefit of suspending a fiber in a filament organizer that may be readily attached to the recoating apparatus with precise fiber to spray head alignment.

A "split sizing die" is a multi-part fiber recoating head that opens to receive an optical fiber, closes to extrude curable recoating material around the surface of a length of fiber and re-opens to release the coated fiber.

The term "shroud" refers to a shield over an ultrasonic spray head to direct a stream of inert gas to entrain and move a cloud of droplets of recoating composition towards a target surface, such as a bare portion of an optical fiber.

The present invention has been developed to provide a process and equipment for conveniently handling a filament in the form of an optical fiber during multiple processing operations that may be at least partially automated as a further benefit to the user. These enhancements and benefits are described in greater detail hereinbelow with respect to the several aspects and alternative embodiments of the present invention.

BRIEF DESCRIPTION OF THE DRAWINGS

FIG. 12 shows a perspective view of a cutting blade according to the present invention for use during mechanical stripping of coating from an optical fiber.

FIG. 13 provides a detail view of a cutting edge of a cutting blade according to the present invention.

FIG. 14 is a detail view showing the relative positioning of a coated optical fiber and the cutting edge of a cutting blade according to the present invention.

DETAILED DESCRIPTION OF THE INVENTION

Figure 1:
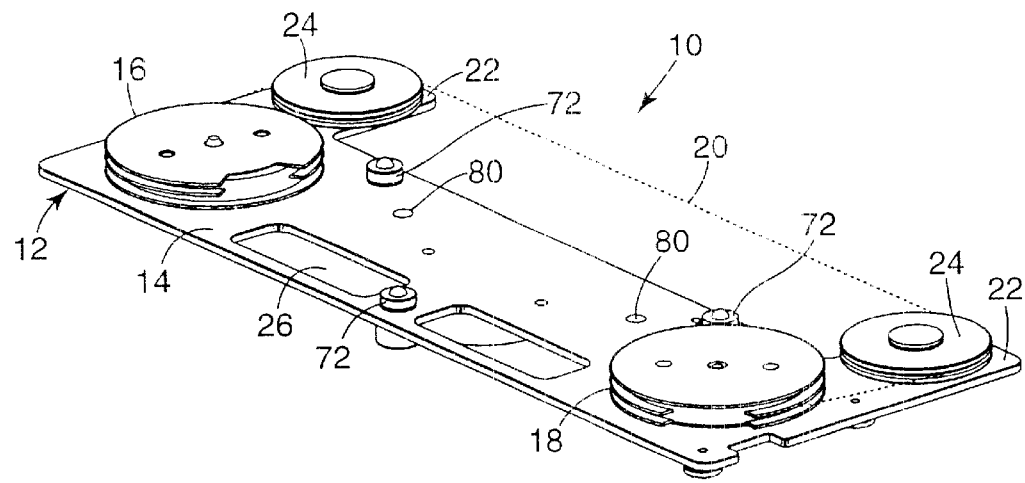
FIG. 1 shows a perspective view of a filament organizer according to the present invention.

Referring to the Figures wherein like numbers refer to like parts throughout the several views. FIG. 1 is a perspective view of a filament organizer 10 including a substantially planar support board 12 that has opposing sides. The support board 12 has, on its first side 14, also referred to herein as its upper side, points of attachment for a lockable spool 16 and a rotary spool 18. Theses spools 16, 18 have a length of filament 20 wound around them and between them. The support board 12 may include mounting plates 22 for one or more guides 24 used to establish a preferred position for a portion of a filament 20 extending from the lockable spool 16 to the rotary spool 18. Attachment of a guide 24 to a mounting plate 22 allows suitable movement of the guide in response to movement of the filament 20.

A support board 12, according to the present invention, optionally includes at least one opening 26 formed therein as a convenient location for holding a support board 12 by hand. An opening 26 preferably occupies a location sufficiently separated from an optical fiber 20 to prevent inadvertent touching of the surface, especially a bare surface of a filament 20, such as an optical fiber. The positioning of an opening 26 has suitable separation from a filament when located between the lockable spool 16 and rotary spool 18 opposite an exposed portion of a filament 20, as illustrated in FIG. 1.

Figure 2:
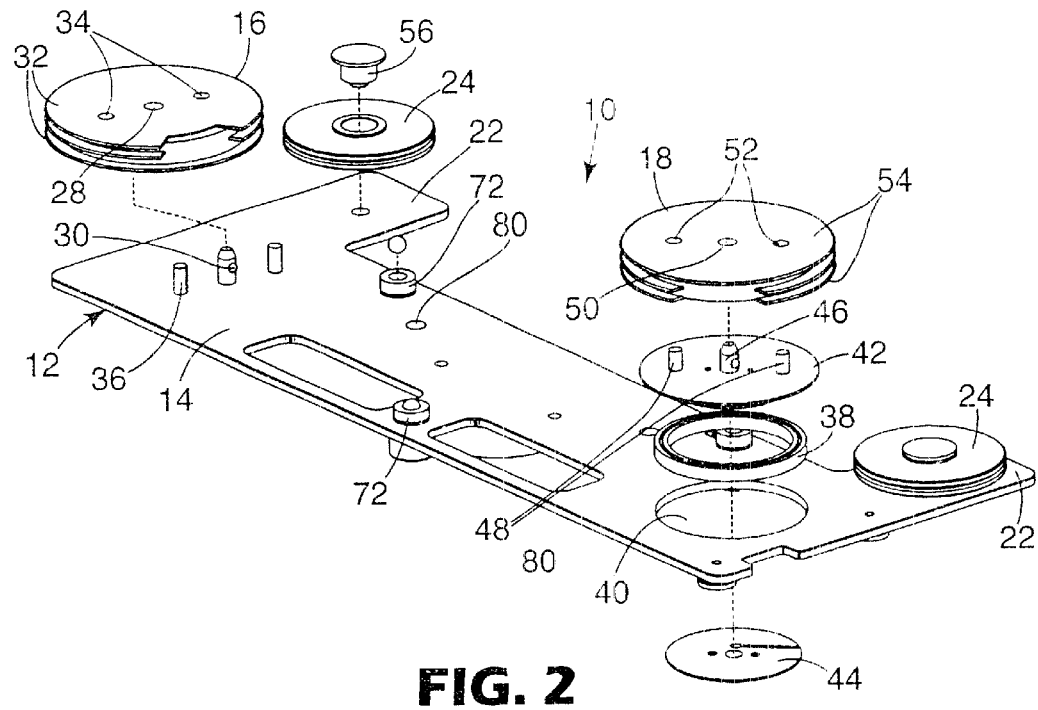
FIG. 2 provides detail portions of a filament organizer according to the present invention in exploded perspective view

FIG. 2 uses a partially exploded view to show detail of an embodiment of a filament organizer 10 according to the present invention. This view depicts how a lockable spool 16, a rotary spool 18, and a pair of guides 24 may be attached to a substantially planar support board 12. As suggested earlier, a computer controlled fiber dispenser may be used to load a prescribed amount of optical fiber between a pair of spools 16, 18. A continuous length of fiber preferably has three sections including a main or central section, several meters in length separating opposite end or pigtail sections, each approximately one meter long. Typically the central section has a length of from about one meter to about six meters. Each of the spools 16, 18 provides storage for an optical fiber pigtail. Filament turns representing pigtail sections are wound on a spool 16, 18 in the same direction as the filament turns of the central section. The spools 16, 18 each include a core divider (see FIG. 4) to separate pigtails from the central section of an optical fiber 20 to facilitate unwinding of pigtails during filament processing.

After fiber loading, the spools 16, 18 are separated and mounted to a support board 12 for fiber storage with a length of filament stretching between the spools 16, 18. One of the spools 16, 18 becomes a lockable spool 16 during sliding engagement between an axial channel 28 in the spool 16 and a post 30 secured to the support board 12. Each faceplate 32 of the lockable spool 16 includes at least a pair of openings 34 positioned on either side of the axial channel 28. The openings 34 align for engagement with a pair of pegs 36 rigidly connected to the support board 12. When the axial channel 28 and openings 34 seat over the post 30 and pegs 36 the lockable spool 16 cannot rotate since the pegs 36 restrict its movement. After mounting the lockable spool 16, as described previously, a change in length of filament 20 between the lockable spool 16 and the rotary spool 18 requires adjustment of a filament 20 by rotating the rotary spool 18. Rotation of the rotary spool 18 relies upon a bearing 38 held by friction in a hub orifice 40 formed in the support board 12 of the filament organizer 10. The bearing 38 facilitates rotation of a spool hub 42 on one side and tensioning hub 44 on the other. The spool hub 42 has a spindle 46 and a pair of pins 48 for alignment with an axial opening 50 and receiving holes 52 in both faceplates 54 of the rotary spool 18. Although held in fixed relationship, the rotary spool 18 and spool hub 42 have rotational freedom provided by the bearing 38.

The embodiment of the present invention illustrated in FIG. 2 includes a pair of guides 24 each taking the form of an idler wheel that rotates around an axle 56. One end of the axle 56 connects to the first side 14 of the support board 12. Filament 20 un-spooling, by rotation of the rotary spool 18, produces sufficient filament 20 between the lockable spool 16 and the rotary spool 18 so that the path of the filament 20 from the lockable spool 16 to the rotary spool 18 passes around each of the idler wheels 24. The resulting assembly, including the filament 20, provides a preferred orientation, as shown in FIG. 1, when the filament 20 is an optical fiber. This orientation places an optical fiber 20 in a readily accessible, spatially precise position for processing, during the manufacture of a fiber Bragg grating, for example.

Figure 3:
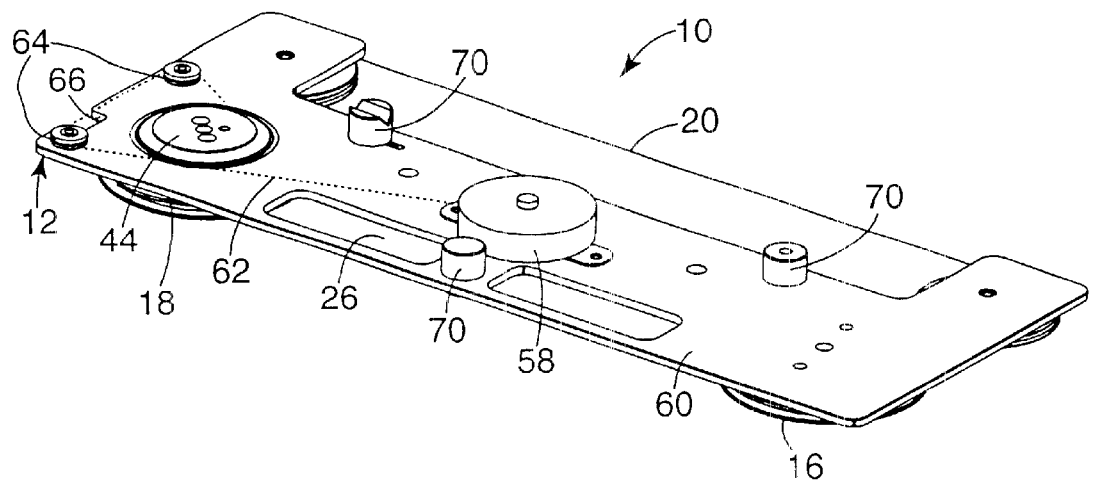
FIG. 3 shows a perspective view of an assembly for applying tension to a filament contained in a filament organizer according to the present invention.

Formation of an optical fiber Bragg grating frequently requires application of tension to a filament 20, i.e. optical fiber, held by a filament organizer 10 according to the present invention. Reference to FIG. 3 indicates one means to apply tension to a filament 20 using a tensioner 58 attached to the lower side 60 of a support board 12. The tensioner 58 applies a constant force to a filament 20 or optical fiber to maintain the filament 20 under slight tension. Force from the tensioner 58 may be transmitted to the filament 20 through a series of components including a tension wire 62 connected between the tensioner 58 and the tensioning hub 44. The tensioning hub 44 acts upon the spool hub 42 because of a direct connection between the two. Movement of the spool hub 42 causes corresponding turning movement of the rotary spool 18 which is centered on the spindle 46 and driven by the movement of pins 48 attached to the spool hub 42. Movement of the rotary spool 18 produces tension in the filament 20 or optical fiber proportional to the constant force produced by the tensioner 58 The tension in the tensioner 58 acts on the tension wire 62 with a force of from 20 g to 200 g. Force distribution through the tension wire 62 and the tensioning hub 44 leads to a resultant force of about 50 g to about 100 g of tension in a filament 20 held in a filament organizer 10. A tensioning hub 44 is typically about half the diameter of a rotary spool 18.

The tension wire 62 may pass unimpeded between the tensioner 58 and the tensioning hub 44. Preferably, however, the location of a section of the tension wire 62 allows access and positional adjustment of the tension wire 62 to remove tension from the filament 20. Removal of the effect of the constant force tensioner 58 uses a force reduction assembly comprising a pair of pulleys 64 on either side of a notch 66 formed in an edge of the support board 12. The tension wire 62, passing around the pulleys 64 and across the notch 66, may be grasped in the vicinity of the notch 66 and extended slightly parallel to the edge of the board 12, and toward the nearest guide 24. Movement of about 1.0 mm to about 2.0 mm releases the tension force applied to a filament 20 by the tensioner 58. Release of tension relaxes a filament 20, in the form of an optical fiber, in preparation to re-tension the fiber. Relaxation and re-tensioning of an optical fiber 20 applies a known and repeatable amount of tension required by the Bragg grating writing process so that resulting optical fiber Bragg gratings will exhibit substantially the same wavelength response.

After installing a filament 20 under tension on a filament organizer 10, a length of filament several meters long may be conveniently carried, in a protected spooled condition, between handling stations, during filament processing. Earlier methods for filament processing required an operator to hand-carry lengths of filament measuring in excess of six meters. Care was required to avoid contact of trailing filament with the floor and other surfaces that could cause contamination and reduction in the yield of manufactured filament devices. A filament organizer 10 according to the present invention may be handheld using the opening 26 in the support board 12. The position of the opening 26 minimizes undesirable inadvertent hand contact with any exposed portion of the filament 20.

Figure 4:
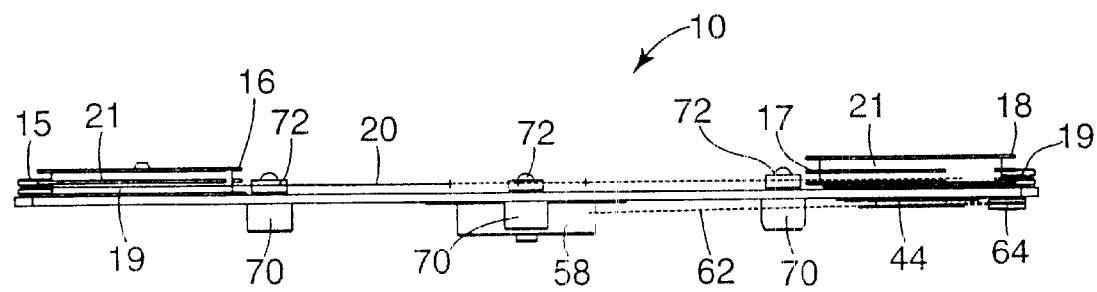
FIG. 4 is a side elevation of a filament organizer.

FIG. 4 shows a side elevation of a filament organizer 10 according to the present invention to indicate the relative positioning of components on the upper 14 and lower 60 side of a support board 12. The figure shows the tensioner 58, spacer blocks 70, tensioning hub 44, tension wire 62 and a pulley 64 on the lower side of the support board 12. The upper side of the support board 12 provides a surface for attachment of organizing mounts 72, a lockable spool 16 and a rotary spool 18 having a filament or optical fiber 20 held under slight tension between them, as described previously. The spools 16, 18 used to store a length of optical fiber 20 are divided spools since the lockable spool 16 includes a dividing wall 15 and the rotary spool has a partitioning wall 17. Part of an optical fiber 20 lying between the spools 16, 18 occupies a lower core 19 of a spool 16, 18 below each of the dividing wall 15 and the partitioning wall 17. This leaves the upper core portion 21 of each spool, i.e. above the dividing wall 15 and the partitioning wall 17 to receive a pigtail end of a continuous length of optical fiber 20. Separation of a central length from the ends or pigtails of an optical fiber 20 using lower 19 and upper 21 core portions of storage spools 16, 18 facilitates unwinding of only the pigtail portions of a fiber 20 during fiber processing.

Figure 5:
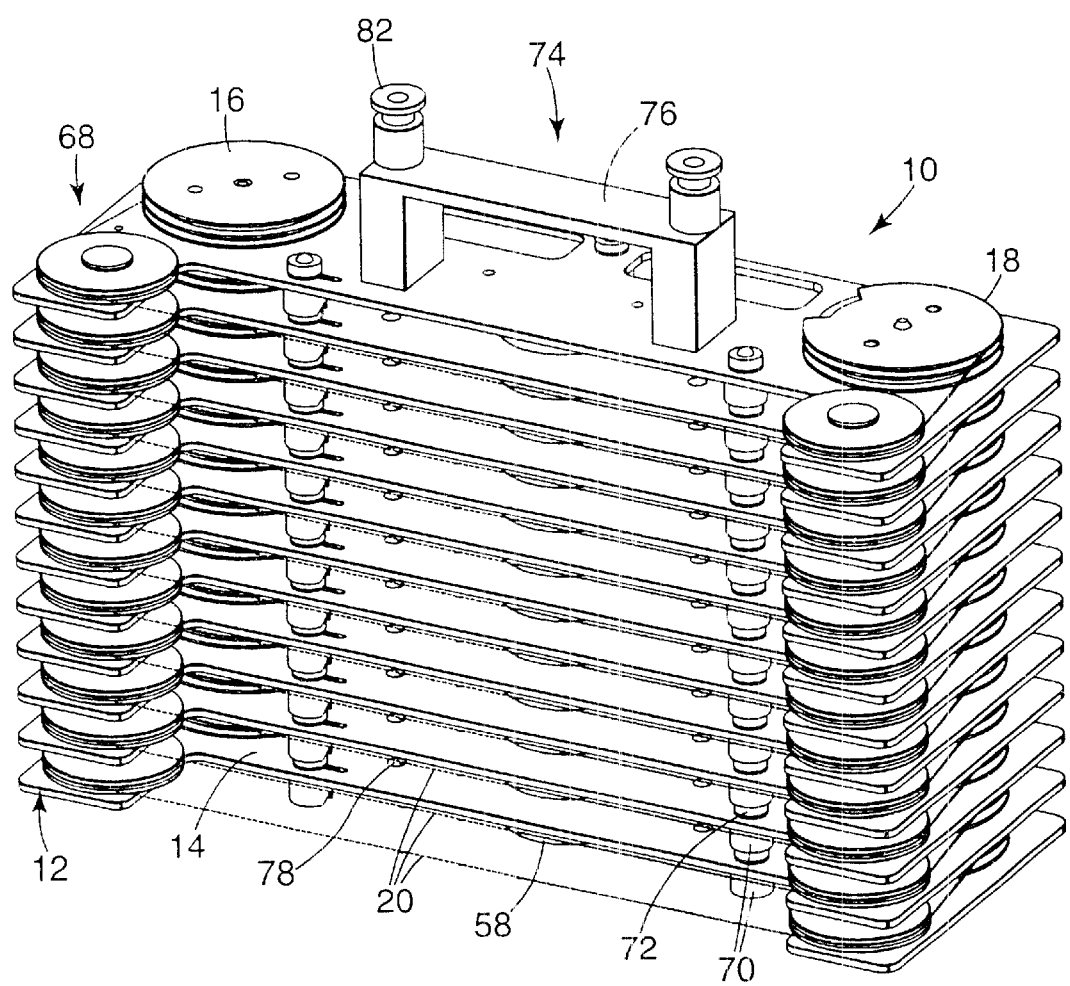
FIG. 5 provides an perspective view of a plurality of filament organizers in a stacked configuration.

With suitable design, two or more filament organizers 10 may be combined to form an assemblage of filament organizers 10. The term, stacked configuration 68, describes herein an assemblage of filament organizers 10, as illustrated in FIG. 5. Design considerations include the placing of stabilizing spacer blocks 70 on the lower surface 60 of a support board 12 for mating registration with organizer mounts 72 positioned on the upper surface 14 of a support board 12. The spacer blocks 70 may have insufficient height to hold a tensioner 58 clear of a planar surface upon which a filament organizer 10 may be placed prior to forming a stacked configuration 68 thereon. This problem may be overcome using a suitably contoured spacer between the lower surface 60 of a support board 12 and the planar surface. Correct stack 68 formation requires addition of filament organizers 10 one on top of another with suitable alignment of downward facing spacer blocks 70 and upward facing organizer mounts 72 to produce a stable stacked configuration 68 by mating registration between filament organizers 10. The combined height of spacer blocks 70 and organizer mounts 72 provides sufficient spacing between filament organizers 10. Alignment of spacer blocks 70 and organizer mounts 72 produces a stacked configuration 68 neatly organizing a number of filaments 20, corresponding to the number of filament organizers 10, in a pre-determined relationship. This relationship facilitates optimum orientation of a stacked configuration 68 with filament processing equipment. The spacing between filaments 20 in a stacked configuration 68 is from about 12.5 mm (0.5 inch) to about 27.5 mm (1.2 inches) preferably about 18 mm (0.7 inch) to about 23 mm (0.9 inch).

Spacer blocks 70 and organizer mounts 72 may be viewed as primary components for aligning one filament organizer 10 relative to its nearest neighbor. Actual fiber 20 positioning and spacing depends upon the location and relative height of the spacer blocks 70 and the organizer mounts 72 on a support board 12. This means that the design of a support board 12 determines the position of a length of filament 20 so that it may be readily located in a stacked configuration 68. In addition to this, a filament 20 occupies a known position on a support board 12 with consistent spacing of the fiber 20 from other portions of the support board 12, such as the mounting plates 22 and upper side 14 and lower side 60 of a support board 12. These features provide reference points for uniting filament organizers 10, 68 to various pieces of apparatus with one or more filaments 10 positioned ready for processing. This provides a filament organizer 10 and a stacked configuration 68 suitable for use in automated filament processing without operator intervention.

Means for handling multiple filament organizers 10 in a stacked configuration 68 includes installation of a stacking connector 74 that optionally includes a carrying handle 76. Preferably a stacking connector 74 comprises one or more rods 78 inserted into through-holes 80 (see FIG. 1) included in a support board 12. A rod 78 may include a flange as a support for the lowest filament organizer 10 in a stacked configuration 68. Alternatively, when a stacking connector 74 comprises additional rods 78 threaded through multiple filament organizers 10, a bracket may be used to connect the ends of rods 78 adjacent to the lower face 60 of the lowest filament organizer 10 in the stack 68. A carrying handle 76 may be attached to a stacking connector 74 by any of a variety of joining methods. Rods 78 protruding from a stacked configuration 68 may include threaded end portions that may be received in tubular openings (not visible) in a carrying handle 76. A threaded nut or similar retainer 82 may secure the handle 76 to the stacking connector 74. This provides a stable stacked configuration 68 of multiple filament organizers 10 that may be carried with ease between stations for processing a plurality of filaments 20 in a single batch or automated operation.

A filament 20 in the form of an optical fiber, once installed in a filament organizer 10, requires a series of steps to produce refractive index modifying features in a selected portion of the optical fiber 20. Optical fiber manufacture, using a draw tower, typically includes the application of protective coatings over the length of the fiber. Identification of protective coatings for optical fibers uses a variety of terms including buffer and coating. The term buffer usually identifies a material coated directly on a bare optical fiber. A coating usually designates a protective material coated over a buffer layer.

Figure 6:
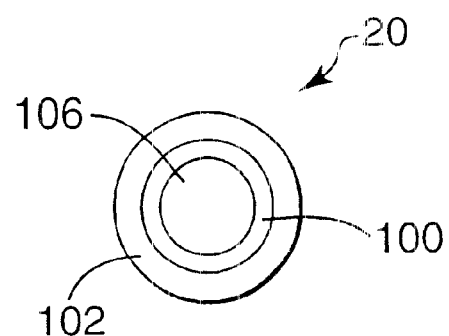
FIG. 6 is a cross sectional view through a dual coated optical fiber.

FIG. 6 is a cross sectional view of an optical fiber showing layers of protective coatings. As used herein the term primary buffer refers to a buffer coating 100 and the term secondary buffer 102 refers to a coating applied to the primary buffer 100. Optical fiber Bragg grating manufacture requires the removal of both the primary buffer 100 and the secondary buffer 102 from a central portion of an optical fiber 20 stored on a filament organizer 10. One method for stripping a buffer coat requires dipping the fiber in a hot concentrated sulfuric acid bath. Preferably the sulfuric acid concentration is at least 95% before heating and stripping the buffer coating 100, 102 from an optical fiber. Acid stripping occurs at a temperature above about 150° C. Damage to a glass core 106 is less likely to occur with acid stripping than with other methods used to remove buffer coats 100, 102, since glass is resistant to acid.

Figure 7:
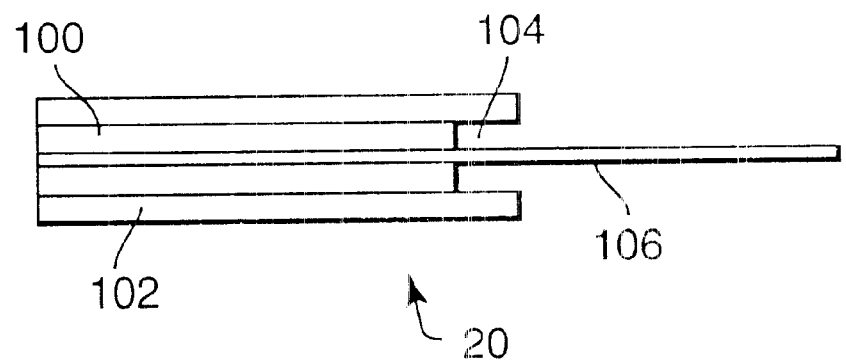
FIG. 7 shows a cross section of a dual coated optical fiber after acid stripping.

A hot acid bath provides an effective medium for removing a single buffer coat, but some types of optical fiber have multiple coatings that may dissolve at different rates. These types of optical fiber may include a relatively insoluble, hard secondary buffer coating 102 over a softer protective primary buffer coating 100, as illustrated in FIG. 6 and FIG. 7. During hot acid stripping, the softer primary buffer coating 100 may dissolve faster than the secondary buffer coating 102. The process of dissolving polymer layers from an bare optical fiber 106 may be accompanied by decomposition due to depolymerizing sulfonation caused by the attack of the concentrated sulfuric acid. Polymer decomposition products may impair the appearance and performance of a modified optical fiber according to the present invention.

Placement of the primary buffer coating 100 under the secondary buffer coating 102 can result in preferential removal by acid of the primary buffer coating 100. Preferential removal of the primary buffer coating 100 produces an undercut 104 below the secondary buffer coating 102 that can collapse inward towards the bare optical fiber 106. As the secondary buffer coating 102 collapses it can trap acid or air bubbles next to the bare optical fiber 106. Entrapment of material including acid, and other liquids or gases, can produce conditions leading to premature failure of an optical fiber 20 for intended applications.

Figure 8:
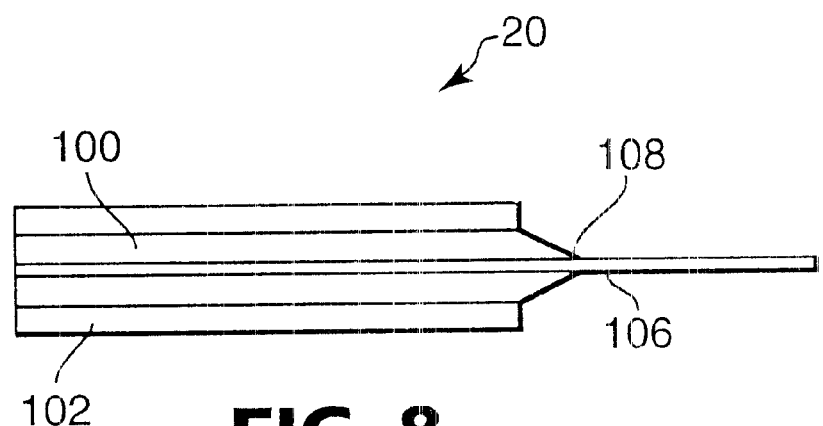
FIG. 8 provides a cross section of a dual coated optical fiber after mechanical stripping to provide a tapered transition.

A contributor to premature failure, as indicated previously, may be the existence of decomposed polymer species after strong acid treatment. This situation may be avoided using an intermediate, mechanical stripping method to provide a cut tapered transition section 108, as shown in FIG. 8, between the primary coating 100 and an bare optical fiber 106. The tapered transition 108 prevents the collapse of a secondary buffer coating 102, as previously described. When mechanical stripping, according to the present invention, precedes acid stripping the formation of a tapered end 108 can present a preferred geometry at the junction between the primary buffer coating 100 and the bare surface of an optical fiber 106.

Figure 9:
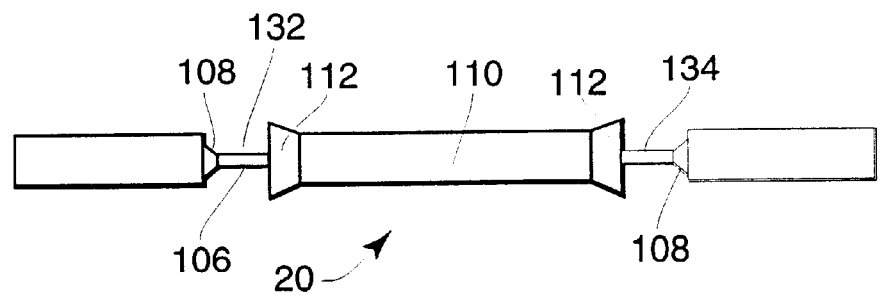
FIG. 9 shows a side elevation of an optical fiber after mechanical stripping to produce a separated central buffer sleeve.

FIG. 9 shows how an intermediate, central portion of an optical fiber 20 may be stripped from two points along its length using a pair of cutting blades. The intermediate portion to be stripped preferably resides in a filament organizer 10 according to the present invention. A mechanical optical fiber stripping apparatus accommodates a filament organizer 10, providing correct orientation for stripping buffer coatings 100,102 from an optical fiber 20. The apparatus controls blades (not shown) that cut into the secondary buffer coating 102 to produce a separated buffer sleeve 110 between a pair of tapered transitions 108 that define the length of bare optical fiber when the primary 100 and secondary 102 buffer coatings have been removed. Each end of the buffer sleeve 110 includes a peeled-back collar 112 that provides a gap for access to the bare surface of the optical fiber 106.

Figure 10:
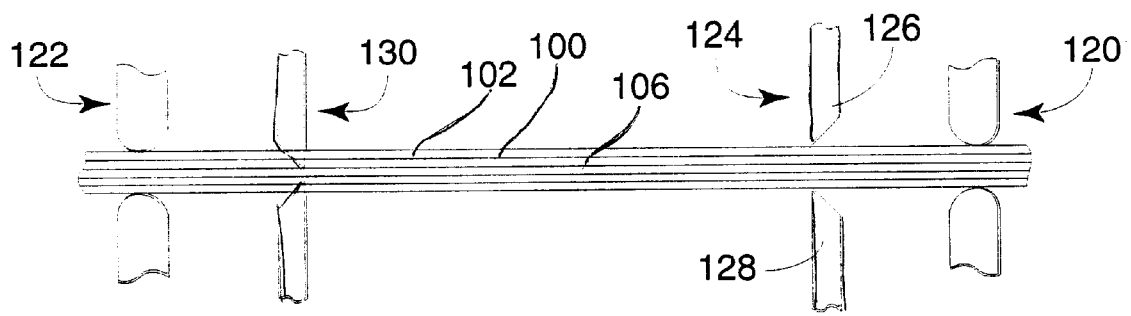
FIG. 10 is a cross sectional view showing a coated optical fiber positioned for mechanical stripping.
Figure 11:
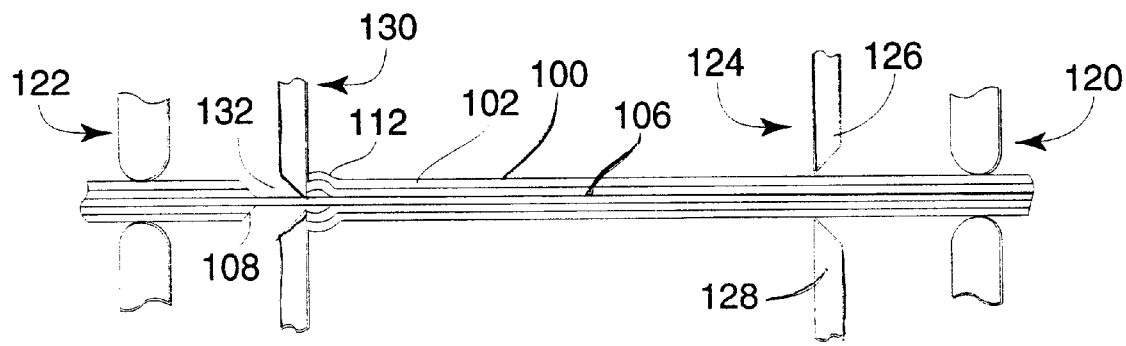
FIG. 11 is a cross sectional view showing a coated optical fiber after formation of a tapered transition

FIG. 10 and FIG. 11 provide clarification of the basic components and steps required for stripping a central portion of a coated optical fiber 20. A first clamp 120 holds one end of a portion of a coated optical fiber 20. The coated optical fiber 20 comprises a fiber core 106 overcoated with one or more protective resin layers 100, 102. A second clamp 122 holds the other end of the portion of the coated optical fiber 20. Both clamps 120, 122 grip the outer surface of a relatively hard secondary buffer coating 102. This prevents damage to the underlying optical fiber core 106. Preferably the clamps 120, 122 include frictional gripping surfaces such as rubber or elastomer gripping surfaces that resist fiber movement during mechanical stripping The immobilized coated optical fiber exists under slight tension, preferably of about 50 g. Typical separation between the first clamp 120 and the second clamp 122 is from about 50.0 mm (2.0 inches) to about 100 mm (4.0 inches) preferably 75.0 mm (3.0 inches) to about 90 mm (3.5 inches). After limiting optical fiber 20 movement between a pair of clamps 120, 122 at least one set of cutting blades 124 may be placed abutting the coated optical fiber 20 with the sharp edge of an upper cutting blade 126 resting against the surface of the coating 102 surrounding the optical fiber 20. The desired position is shown by the location of a first set of cutting blades 124 relative to the clamped, coated optical fiber 20. A second set of cutting blades 130 is shown in FIG. 10 in a position, adopted by the cutting blades 130, after penetration of the secondary buffer 102 of an optical fiber 20. Each set of cutting blades includes an upper blade 126 and a lower blade 128. The sharp edge of each cutting blade 126, 128 includes at least one notch having a radius in common with any primary buffer coat 100 applied to an bare optical fiber 106. During fiber stripping, the upper 126 and lower 128 blades move inwards, as shown for the second set of cutting blades 130, cutting through the secondary buffer 102 until they touch one another, before penetrating the primary buffer 100. The distance between the first set of cutting blades 124 and the second set of cutting blades 130, at this point, is typically between about 30 mm (1.2 inches) and about 40 mm (1.5 inches). After cutting through an outer or secondary buffer coating 102, application of suitable force moves the second set of cutting blades 130 closer to the first set of cutting blades 124 and parallel to the axis of the optical fiber 20. This transverse movement of the second set of blades 130 generates a stripping action that results in a gap 132 in the coating around the optical fiber core 106. The stripping action exposes a bare fiber portion 106 in the gap 132. One side of this gap 132 has a contoured, tapered transition 108, in the primary buffer 100, from the bare optical fiber 106 to the secondary buffer coating 102. The other side of the gap includes a compressed, peeled-back collar 112 of stripped coating 100, 102. When the cutting and stripping operations have been completed at one end of the coated optical fiber portion, the opposite end of the fiber 20 may be stripped by initiation of cutting action of the first set of cutting blades 124. This produces a second gap 134 in the coating around the bare fiber 106, as illustrated in FIG. 9. The second gap 134 includes a similar tapered transition 108 to that produced by the cutting action of the second set of cutting blades 130.

Application of acid stripping to a mechanically stripped fiber, as in FIG. 9, preferably exposes only the buffer sleeve 110 to acid attack. As long as the tapered ends 108, also referred to herein as tapered transitions, remain out of the strong aqueous acid they remain free from attack and chemically unchanged. In this condition the tapered transitions 108 have a surface energy more compatible with recoating compositions. This allows the recoating compositions to readily wet the surface of the tapered transitions 108 following modification of the central portion of a filament. Surface compatibility and ready wetting by recoating compositions produces defect free junctions between previously coated and recoated sections of optical fibers. The existence of defects, e.g. air bubbles, in transition areas of an optical fiber may adversely affect the mechanical strength and light transmission characteristics of an optical fiber device, rendering it unsuitable for its intended use.

FIG. 12 shows the design of blade components used for cutting the secondary buffer coating 102 and displacing the primary buffer coating 100 to cause separation of the primary buffer coating 100 from a bare optical fiber 106. As illustrated in FIG. 12, a blade 140 provides detail of features that may be included in both sets of cutting blades 124, 130. The blade includes provision for stripping several optical fibers 20 simultaneously. It will be appreciated that the same blade 140 may be used to strip single or multiple fibers 20 depending on the number of filament organizers 10 inserted into the stripping apparatus (see FIG. 17).

Figure 15:
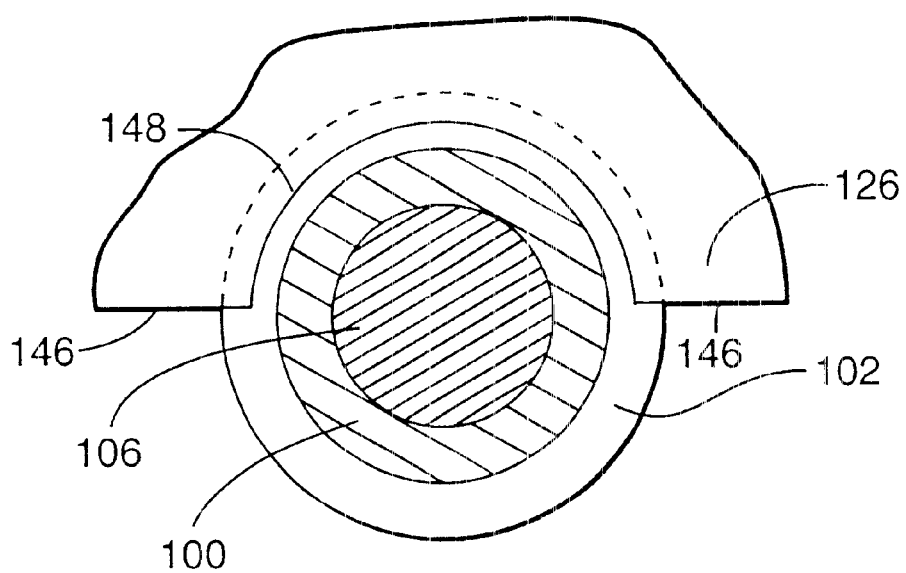
FIG. 15 is a cross sectional view indicating the depth of cut of a cutting edge, and positioning of an upper blade that has penetrated a secondary buffer around an optical fiber.
Figure 16:
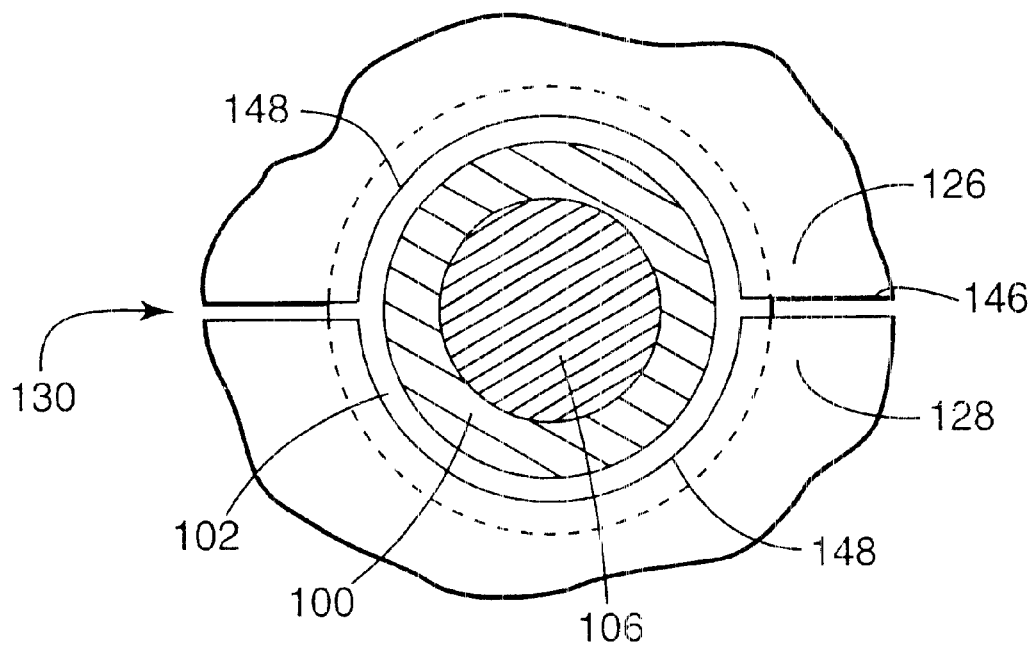
FIG. 16 provides a cross sectional view showing depth of cut of an upper blade and a lower blade during mechanical stripping of secondary buffer from an optical fiber.

A stripping blade 140 according to the present invention includes at least one bevel 142 as a portion of the blade 140 that includes several channels 144 machined into its surface. The channels 144 open to an edge 146 of a bevel 142 as sharpened notches 148 having approximately circular cross-section when viewed from the side opposite the bevel 142, as in FIG. 14. A detail view, shown in FIG. 13 provides clarification of the structure of the bevel 142 including the channels 144 machined therein. A coated optical fiber 20 is included in FIG. 14 to indicate its preferred position before penetration of the secondary buffer 102 by a sharpened notch 148 of a cutting blade 140. The knife-edge of a sharpened notch 148 preferably reaches only towards the outer surface of the primary coating 100 of an optical fiber 20 without cutting into it. When used for stripping coating from an optical fiber 20, the notches 148 cut a circular path around an optical fiber core 106 as shown in FIG. 15 and FIG. 16. In the illustration of FIG. 15 a sharpened notch 148 appears as it would after an upper cutting blade 126 penetrates the secondary buffer 102 of an optical fiber 20. This relates to the position of the second set of cutting blades 130 as shown in FIG. 10. The relationship between the upper blade 126 and lower blade 128 of the second set of cutting blades 130 appears in the diagrammatic representation shown in FIG. 16. The sharpened notches 148 of the upper blade 126 and lower blade 128 have penetrated the secondary buffer coating 102 without reaching the surface of the primary buffer coating 100. Since the advancing edges 146 of the blades 126, 128 have made contact there can be no further advancement of either blade 126, 128.

Stripping blades 126, 128 according to the present invention perform biaxial movement. Initial movement of a blade 126, towards a fiber core, produces a cut as a blade penetrates the secondary buffer coating 102 of the fiber 20. After traveling the thickness of the secondary buffer coating 102, the blade begins to move toward the center of the optical fiber 20, parallel to its axis. This movement disrupts the coating 100, 102, producing a taper 108 clearly visible in the softer primary buffer coating 100. In certain cases, the taper may also extend into the secondary buffer layer as shown in FIG. 11. The taper 108 provides a conical boundary separating the bare optical fiber 106 from the overlying buffer structure 100,102.

As described, the mechanical stripping apparatus includes two sets of vertically opening and closing cutting blades 124, 130 adapted for vertical, then horizontal movement either independently or simultaneously. A pair of clamps 120, 122, on either side of the cutting blades 124, 130, holds a strippable filament in a taught condition during the stripping process. Another embodiment of a mechanical stripping apparatus alters the angle of the incision during the cutting process to modify the shape of a tapered transition 108. As the blades 124, 130 close towards the coating 100, 102 around a clamped fiber 20 an angled surface or biasing cam surface deflects the path of the blades to a prescribed entry angle into the coating 102 so as to provide a controlled tapered transition. This produces an intentionally angled cut by moving the blades 124, 130 diagonally into the coating. Any change in the angle of the cam surface produces a corresponding change in the angle of a tapered transition 108 to allow consistently reproducible contours of a coating 100, 102 abutting either side of a bare portion of an optical fiber. Suitable selection of the cam angle produces tapered transitions 108 having contours and dimensions facilitating essentially defect-free recoating of bare optical fiber portions. Successful mechanical stripping to provide a tapered transition may proceed under ambient conditions, as indicated previously. With some buffers, however, the modulus of the buffer resin is in a range that complicates the formation of a tapered transition. In such cases, it may be necessary to soften the resin by heat or chemical action before attempting the mechanical stripping process to produce the desired tapered transition.

Completion of the mechanical process of fiber stripping leaves a central portion of an optical fiber 20 having a central sleeve 110 of protective buffer coating 100, 102 that has been separated from the remainder of the buffer coating 100, 102 over the optical fiber core 106. Opposing gaps 132, 134 between the sleeve 110 and remainder of the buffer coating 100, 102 provide points for hot acid to penetrate under the central sleeve 110 to facilitate removal of the sleeve 110, which dissolves in hot acid. Preferably the acid does not reach the tapered transitions 108 of a previously mechanically stripped coated optical fiber 20. Removal of the central sleeve 110, as a solution in hot acid, followed by rinsing in water and alcohol, leaves a clean, bare portion of an optical fiber 106 in suitable condition for further processing. Depending on the effectiveness of mechanical stripping, much of the disrupted buffer sleeve 110 may be lifted from the bare fiber portion. This reduces the amount of buffer coating to be dissolved from a fiber 20 during acid stripping.

Figure 17:
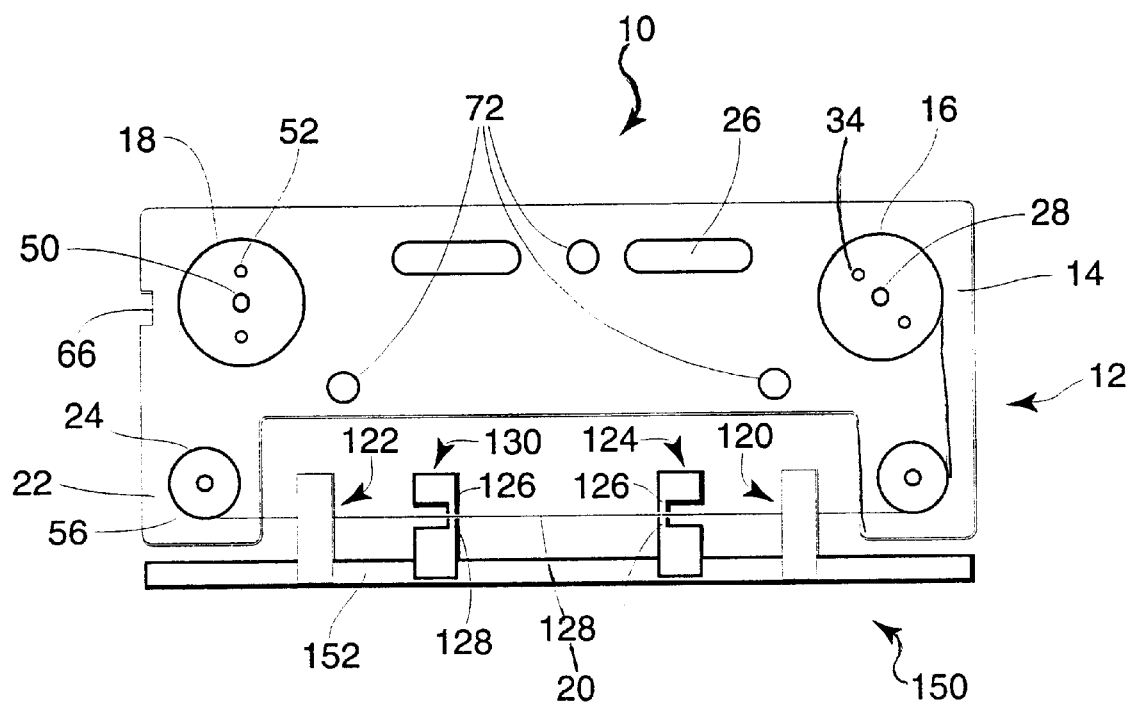
FIG. 17 is a diagrammatic representation of a side elevation showing the relative positioning of a filament organizer and mechanical stripping apparatus according to the present invention.

Stripping of protective buffer coating from an optical fiber 20 may be conducted as an automated or semi-automated process using equipment suitably designed for the task. Preferably design of the equipment allows processing of multiple fibers 20 in a single operation. FIG. 17 shows the positioning of a filament organizer 10 relative to a mechanical stripping apparatus 150. A mechanical stripping apparatus 150 according to the present invention includes a base 152 as a mounting platform for optical fiber clamps 120, 122 and sets of cutting blades 124, 130. Optical fiber clamps 120, 122 may either move relative to the base 152 or be secured thereto. Optional securing of the clamps 120, 122 facilitates mechanical stripping with a fiber 20 either at its original tension, set by the filament organizer 10, or under tension produced by moveable clamps 120, 122.

The sets of cutting blades 124, 130 slidably engage the surface of the base 152. Slidable engagement of the sets of cutting blades 124, 130 facilitates the axial movement of the blades 124, 130 to form a tapered transition 108, as previously described. A filament organizer 10 may be suspended by any suitable method relative to the mechanical stripping apparatus 150 provided that the filament 20, clamps 120, 122 and cutting blades 124,130 have alignment on a common axis.

After the preliminary step of mechanically stripping the central portion of a fiber 20, acid stripping may require formation of a loop, suspended from a filament organizer 10. The suspended loop may be submerged in hot concentrated sulfuric acid. An acid bath is a convenient and clean method to remove the buffer coat from acid-resistant glass.

A known method uses acid to remove protective coatings from optical fibers. The method requires handling of fibers each individually as much as six to eight meters long. Handling of such optical fibers requires caution because of the small diameter and transparency of the filamentary structure. If the optical fiber snags an object during handling, the glass fiber core could fracture without showing immediate evidence of damage.

Figure 18:
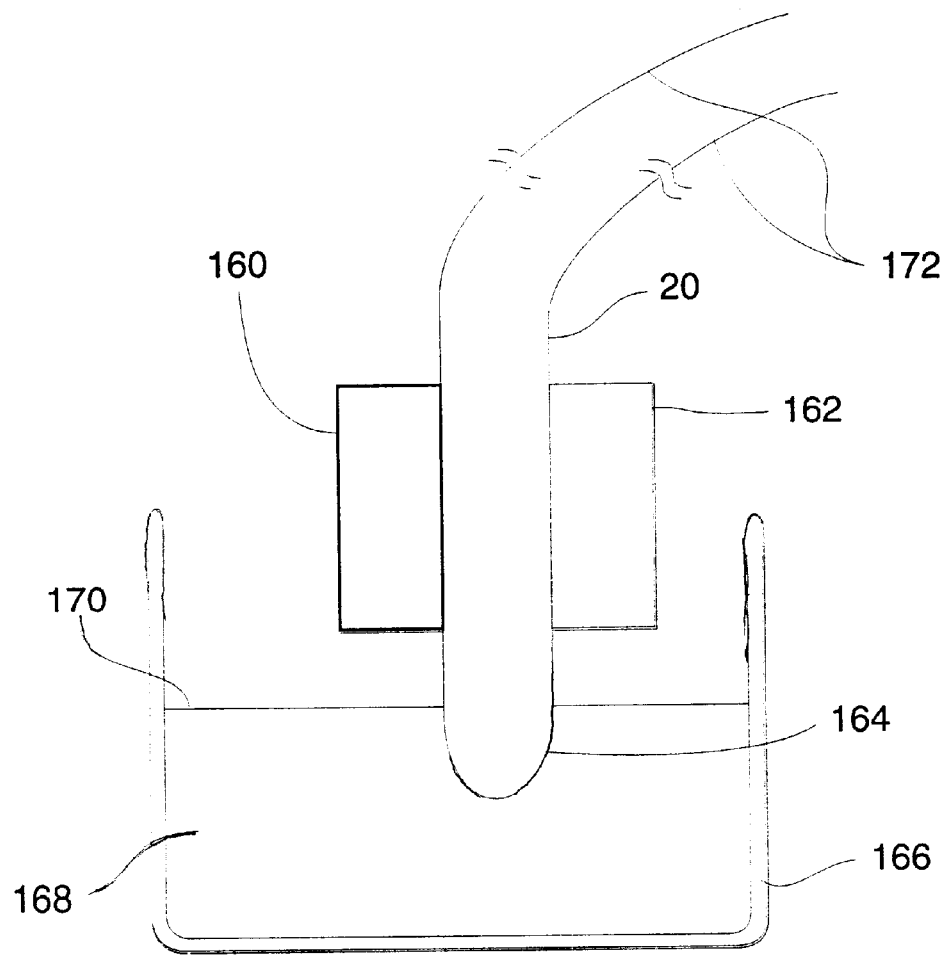
FIG. 18 provides a cross sectional view of a coated optical fiber loop during removal of coating by immersion in acid contained in an acid bath.

A manual method for loop formation includes extending an optical fiber over two blocks having a distance of separation of about six inches. The folding of a first block 160 over a second block 162 produces a loop 164, shown by the diagram of FIG. 18. This figure also includes an acid bath 166 with capability to suspend the blocks 160,162 and loop 164 in suitable position for acid 168, preferably sulfuric acid, to dissolve protective buffer coatings 100, 102 from the U-shaped loop 164. The length of coating 100, 102 removed from an optical fiber 20 will depend upon the depth to which the optical fiber loop 164 extends below the surface 170 of the acid.

Loops having substantially a desired size and shape form relatively easily, but individual fibers need careful handling to avoid damage to exposed glass surfaces. The "U" shaped loop 164 of fiber 20 lies on one side of a pair of blocks 160,162 with relatively long trailing fiber ends 172 extending from the opposite side of the blocks 160,162. In this arrangement the loop 164 and the fiber ends 172 are at risk for breakage or related damage. Damage occurs in different ways including inadvertent contact or impact during fiber processing operations including acid removal of buffer coating 100, 102 from the fiber 20, fiber Bragg grating writing, fiber annealing, fiber recoating and the like. This problem may now be avoided using filament organizers 10 according to the present invention. Filament in the form of optical fiber 20 is readily loaded onto filament organizers 10 without damage. Also the design of a filament organizer 10 allows stacking of multiple organizers to increase process throughput. A stacked configuration 68 of filament organizers places filaments, i.e. optical fibers 20, in a suitably spaced-apart relationship for processing from fiber stripping to fiber Bragg grating recoating, as further described below.

Figure 19:
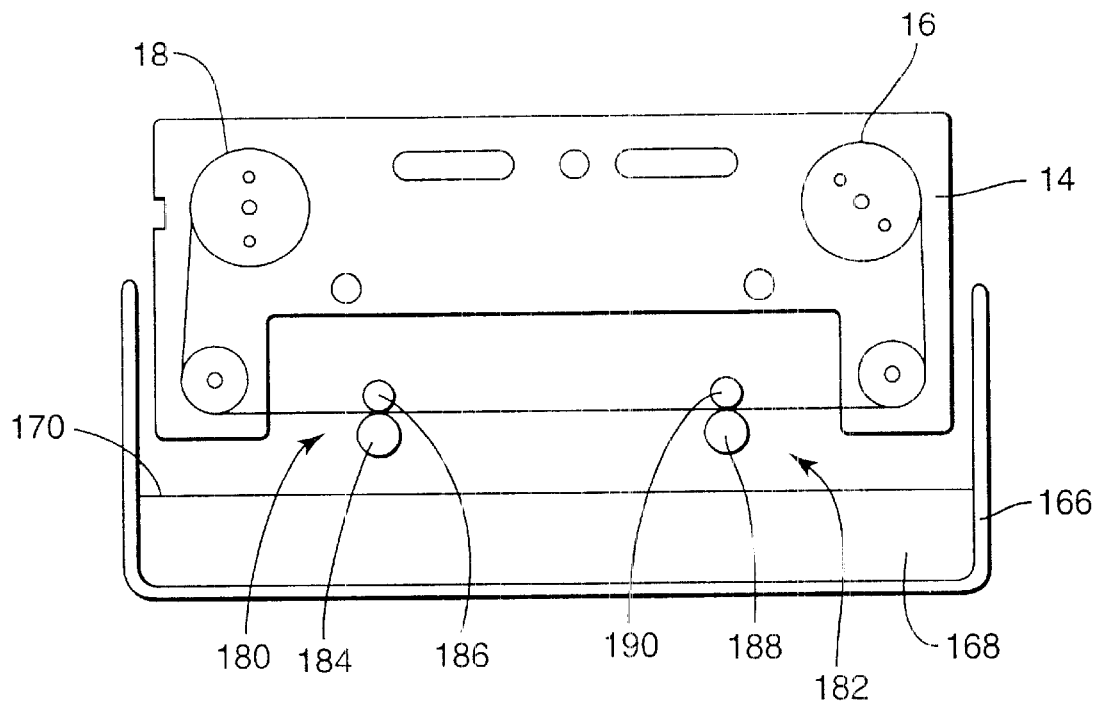
FIG. 19 is partial cross section showing the relative positioning of a filament organizer according to the present invention and an acid-containing bath before formation of an optical fiber loop.
Figure 20:
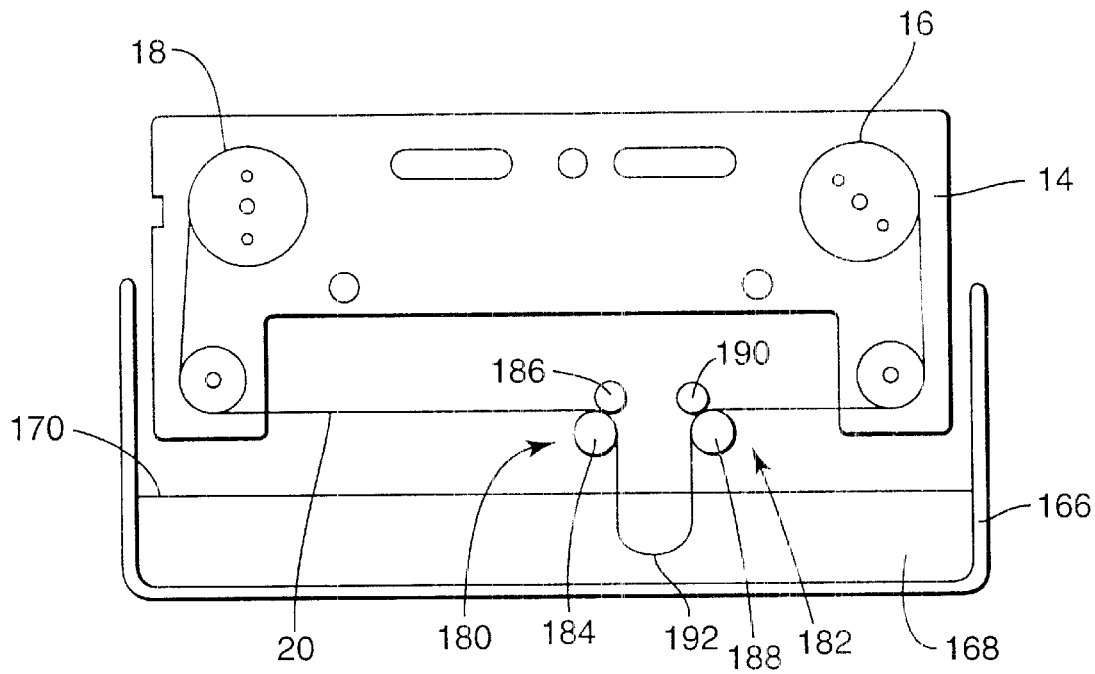
FIG. 20 is partial cross section showing the relative positioning of a filament organizer according to the present invention including a loop suspended from the filament organizer for immersion of an arcuate portion of the loop below the acid surface.

FIG. 19 indicates arrangement of a filament organizer 10 for acid stripping using an apparatus that will reposition an optical fiber 20 in a filament organizer 10 to produce a suspended optical fiber loop similar to the previously described loop 164 formation between blocks 160, 162. The apparatus grips the coated optical fiber 20 at two points along its length as indicated in FIG. 19. A loop forms when these two points move toward each other, as shown in FIG. 20. The fiber is held at one point between a first pair of rolls 180 and at a second point by a second pair of rolls 182. A layer of elastomer covers a lower roll 184, 188 of each pair of rolls 180, 182. Each roll diameter is based on the minimum advisable fiber bend diameter to avoid inducing damaging bending stress during optical fiber manipulation to form a loop. The elastomer provides compliance to lower contact stress, reduce fiber slip, and hold multiple fibers simultaneously.

Each pair of rolls 180,182 converges to pinch the fiber 20. Next, the upper roll 186, 190 of each pair rotates toward each other, inducing a shallow bend in the fiber 20. The shallow bend establishes a plane to be occupied by a machine-formed loop when the pairs of rolls 180, 182 move toward each other. The looping method works with the fiber tray 10 by using two removable upper rolls 186, 190 and two non-removable lower rolls 184, 188.

The present invention, in one of its embodiments, facilitates the process of acid stripping of multiple fibers in a single operation. Successful processing of multiple fibers requires several features that are possible using filament organizers according to the present invention. Of particular importance is the use of a tool that shapes optical fiber into loops while minimizing the possibility of fiber damage. A suitable loop-shaping tool produces loops with repeatable size and shape. Once formed, loops preferably do not bend out of plane. This latter feature is important to the processing of multiple fibers that would tend to interfere with each other if out-of-plane bending occurred. Also, loops formed using stacked configurations of multiple fibers possess substantially the same size and shape, as required for automated and/or semi-automated processing.

Figure 21:
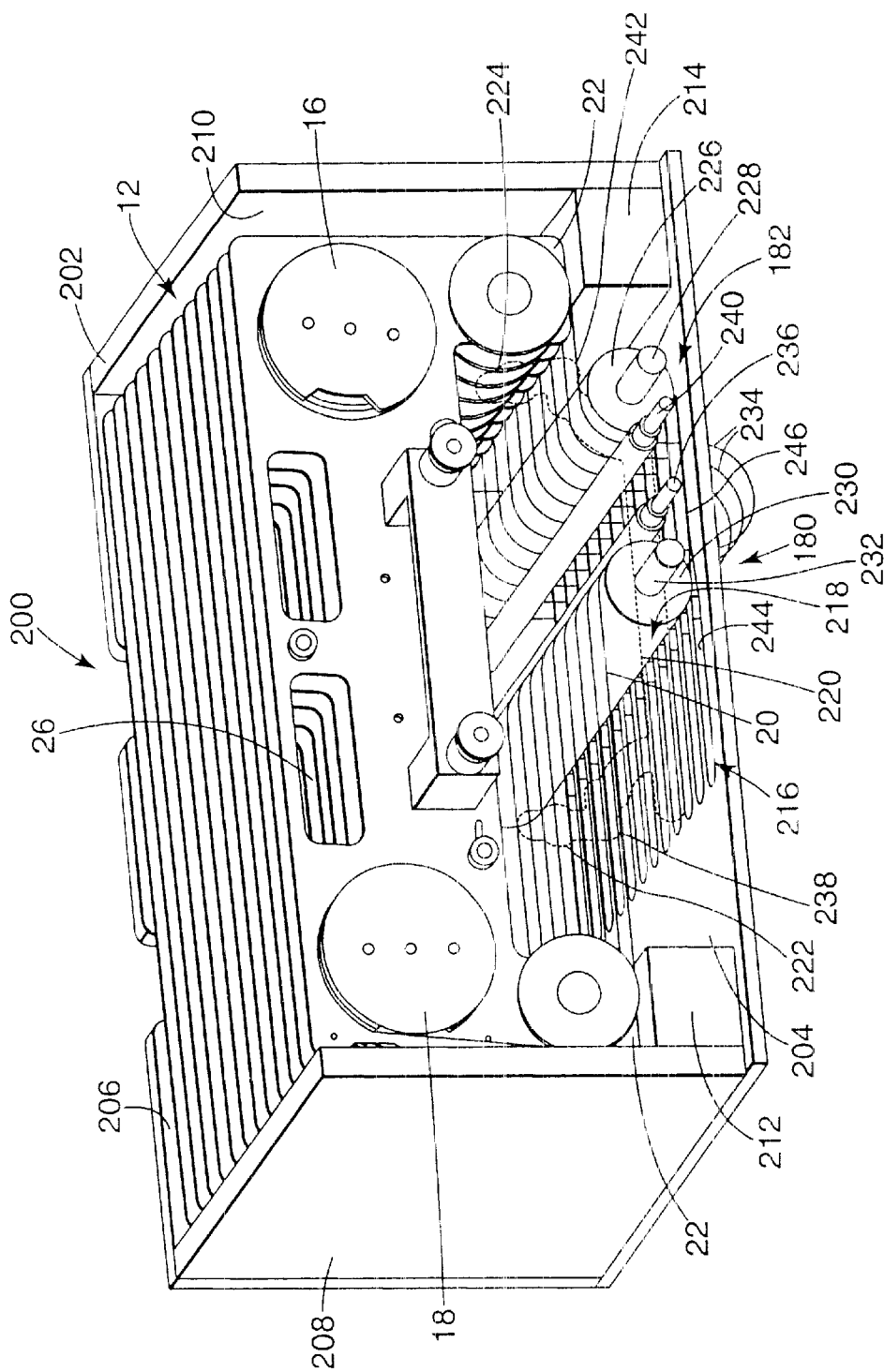
FIG. 21 is a perspective view including a cutaway section to show internal detail of a loop former for a stacked configuration of filament organizers.

FIG. 21 shows a perspective view of a loop former 200 according to the present invention including detail of the position of a stacked configuration 68 of filament organizers 10 inside a loop forming container 202. The loop-forming container 202 is essentially a closed box including a floor 204, a front wall (not shown), a rear wall 206 and first 208 and second 210 sidewalls. Inside the container 202, a first ledge 212 occupies a position adjacent the junction between the first sidewall 208 and the floor 204. A second ledge 214 occupies a similar position adjacent the junction of the second sidewall 210 and the floor 204. The floor 204 includes a plurality of longitudinal slits 216 disposed orthogonally towards the first 212 and second 214 ledges. Each of the front wall and the rear wall 206 includes a generally U-shaped guide slot 218 that is indicated in dotted line form in FIG. 21. Preferably the guide slot 218 includes a horizontal slot 220 joined to an angled slot 222, at one end, and an opposed angled slot 224 at the other. A seated roller 226 includes an axle 228 engaging one end of the horizontal slot 220 in the front and rear 206 walls of the loop-forming container 202. The seated roller 226 preferably has a covering of an elastomeric material. A movable roller 230 includes axle ends 232 extending into the horizontal slot 220 at the front and rear 206 walls. The movable roller 230 is repositionable along the length of the horizontal slot 220 to facilitate formation of multiple extended loops 234 from a stacked configuration 68 of filament organizers 10 positioned in the loop-forming container 202.

The loop former 200 provides accommodation for a stacked configuration 68 of filament organizers 10. Installation of a stacked configuration 68 inside a loop-forming container 202 requires orientation of the stacked configuration 68 to provide alignment of filaments 20 with the plurality of slits 216 in the floor 204 of the container 202. This may be accomplished by holding a stacked configuration 68 by the openings 26 in support boards 12 followed by lowering the stacked configuration 68 into the loop-forming container 202 until the mounting plates 22 of the filament organizers 10 rest on the first 212 and second 214 ledges, as shown in FIG. 21. The stacked configuration 68 is installed with the seated roller 226 and movable roller 230 at opposite ends of the horizontal slot 220. Correct positioning of the stacked configuration 68 relative to the seated 226 and movable 230 rollers provides gentle contact between each filament 20 and the surfaces of the rollers 226, 230. In this condition, the filaments 20 should still be under tension and free from bends.

Having positioned the stacked configuration 68 in the loop-forming container 202 with the filaments 20 touching the fully separated rollers 226, 230 a first rod 236 inserted through the angled slot 222, of the front wall, extends across the container 202 to enter the angled slot 222 in the rear wall 206 of the loop forming container 202. After insertion, the first rod 236 occupies a step 238 of the angled slot 222. A second rod 240 similarly positioned, in a notch 242 of the opposed angled slot 224, completes formation of the first pair 180 and second pair 182 of rolls. Movement of the first 236 and second 240 rods to follow the contours of the angled slot 222 and the opposed angled slot 224 initially establishes contact between the rods 236, 240 and the filaments 20. An elastomer band stretched over the ends of each pair of rolls 180, 182 draws the rolls together to increase their gripping force on the filaments 20. With continued gentle urging, the rods 236,240 continue movement towards the horizontal slot 220. This movement places the rods 236,240 side by side with the corresponding rollers 230, 226 at each end of the horizontal slot 220. During this movement the filaments 20 begin to wrap around the rollers 226, 230 in response to downward force applied by the rods 236,240. The applied force also draws filament from each rotary spool 18 with the resulting formation of preformed loops having a height approximately equal to the diameter of the rods 236, 240. Preformed loops become extended loops 234 of greater height through movement of the first pair of rolls 180 towards the second pair of rolls 182. This creates an exposed loop 234 protruding through each slit 216 in the floor 204 of the loop-forming container 202. By design, the slits 216 limit the amount of out-of-plane bending by the filaments 20. Design features of each slit 216 include a loop entry 244 about 15.0 mm (0.625 inch) wide, and a narrower loop station 246, having a width of about 1.6 mm (0.064 inch). The loop entry 244 is wider than the loop station 246 to prevent contact of the mechanically stripped fiber portion of an optical fiber 20 with the sides or other parts of a slit 216 during the initial stages of exposed, extended loop 234 formation. As the height of the loop 234 increases, the mechanically stripped portion of the fiber emerges below the floor 204 of the loop-forming container 202. Any optical fiber 20 residing in a slit 216, at this point, has a covering of buffer coating to protect the optical fiber from contact with any of the slit 216 surfaces. Thus, protected, the looped optical fiber 234 enters the narrow loop station 246 where it will stay during removal of residual primary and secondary buffer coatings by acid stripping. The loop entry 244 opens to the upper and lower surfaces of the floor 204 of the loop-forming container 202. Preferably the opening to the upper surface of the floor 204 is wider (15.0 mm) than the opening (12.5 mm) to the lower surface of the floor 204. This description indicates that the loop entry 244 of each slit 216 has a somewhat V-shaped cross section to assist in controlling the spatial positioning of each exposed, extended loop 234. Loop control provided by each narrow loop station 246 counteracts torsional stresses introduced during manufacture of filaments 20 in the form of optical fibers. It will be readily appreciated that each extended loop 234 hangs below the floor 204 of the loop-forming container 202 ready for immersion in an acid-containing bath 166 as indicated in FIG. 20.

Figure 22:
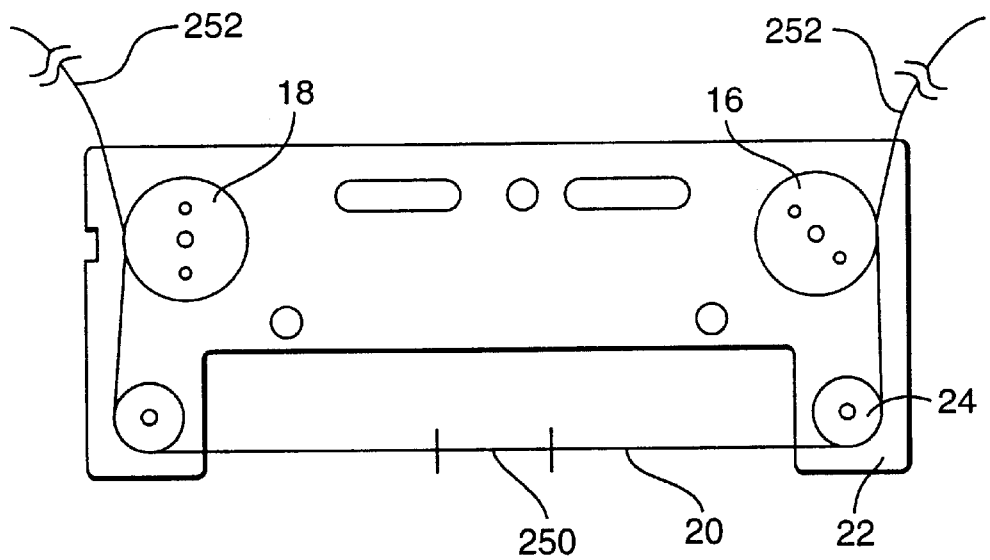
FIG. 22 provides a side elevational view of a filament organizer according to the present invention wherein pigtail portions of filament have been unwound from storage reels.

FIG. 22 shows the condition of an optical fiber 20 after the process steps of mechanical stripping, and acid stripping to provide a length of an optical fiber 20 having a buffer-free bare central portion 250 suitably prepared for refractive index modification associated with the writing of a Bragg grating. Before the actual writing of a grating occurs, the unspooling of an end section of fiber provides an optical fiber pigtail 252 suitable for the formation of splices or connections between optical fibers 20. At this point in the process, a pigtail 252 at each end of the optical fiber, carried on the filament organizer 10, provides a point of connection so that the progress and accuracy of grating writing may be optically monitored during the writing process.

Optical fiber Bragg gratings may be written in a plurality of optical fibers 20 each having a bare central portion 250. Convenient handling of these fibers 20 uses filament organizers 10 in a stacked configuration 68 according to the present invention. The pigtails 252 of each optical fiber 20 require positioning using fixtures to permit accurate alignment of fiber ends with equipment that monitors the progress of fiber Bragg grating writing. The fixture is an optical fiber connector including a central body with opposing fiber receiving ends. The monitoring equipment may use optical fiber or non-contact coupling to the pigtail ends to complete the optical circuit. Connection to fibers 20 from each filament organizer 10 in a stacked configuration 68 uses pigtail ends adapted to plug into the connector. A connector may accommodate pigtail ends of a single optical fiber 20 or a plurality of fibers 20 having pigtail ends previously terminated to the requirements of a multi-fiber connector. The term "ribbonized" has been applied to one form of termination wherein the ends of pigtail sections of fiber lie side by side to form a single layer of fibers having a flat ribbon-like appearance. Positioning of the pigtail ends allows them to mate with a multi-fiber connector.

Figure 23:
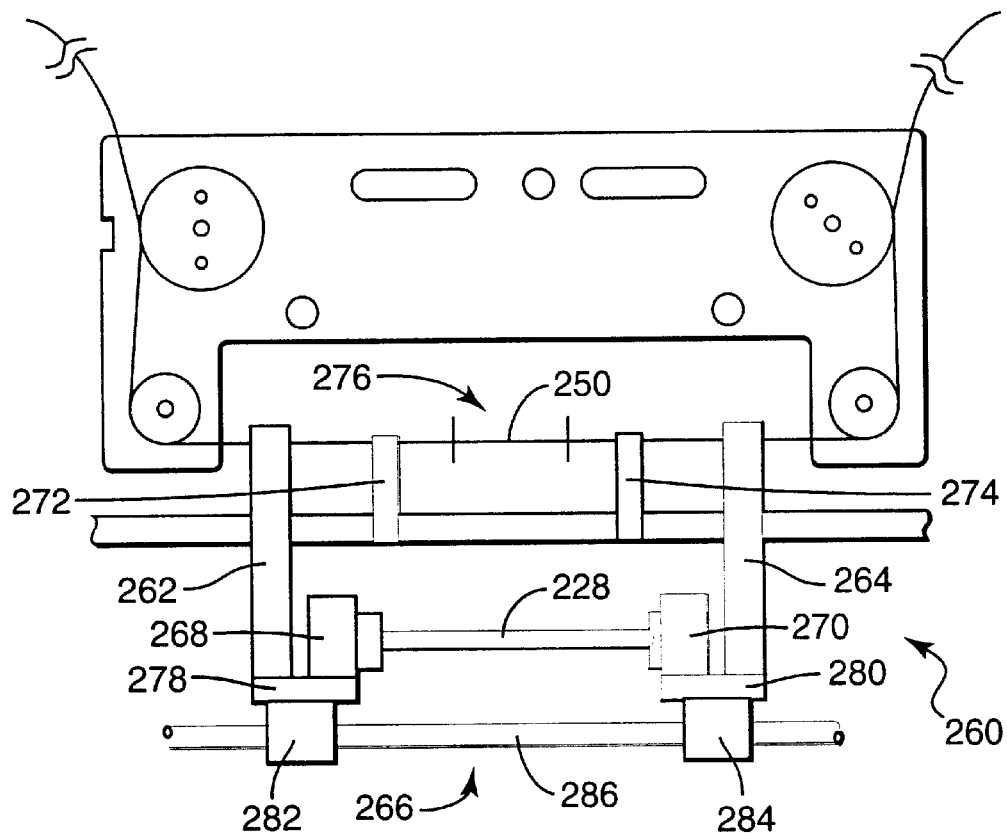
FIG. 23 is a diagrammatic side elevation of a filament organizer according to the present invention positioned in a voice-coil tensioning device during modification of a stripped portion of an optical fiber.

FIG. 23 indicates a filament tensioning apparatus 260 used for further processing of an optical fiber 20 held in a filament organizer 10 according to the present invention. After placement of an optical fiber 20 on a support board 12, as discussed previously, the portion located between the mounting plates 22 of the filament organizer 10 exists in a condition of tension applied by a tensioner 58. In preparation for the writing of a grating, the tension wire 62, of a selected filament organizer 10 (see FIG. 3), may be grasped in the vicinity of the notch 66 and extended slightly parallel to the edge of the board 12, and toward the nearest guide 24. Movement of about 1.0 mm to about 2.0 mm releases the tension force applied to a filament 20 by the tensioner 58. Preferably the filament organizer 10 is one of a stacked configuration 68 positioned on a platform of an indexing unit. The indexing unit raises and lowers the stacked configuration 68 using any one of a variety of mechanical and hydraulic structures. In one embodiment, sliding engagement of the platform with one or more vertical posts or beams allows upward and downward movement of the platform and stacked configuration it supports. The platform may include organizing mounts for mating engagement with spacer blocks on the lowest filament organizer so that the stacked configuration 68 is suitably aligned with the optical fiber 20, of each filament organizer, accessible to a fiber tensioning apparatus 260.

The indexing unit remains stationary during the approach of a fiber tensioning apparatus 260 to apply clamps and grippers to a central portion of each optical fiber 20 in a stacked configuration 68. Approach of the fiber tensioning apparatus 260 may be facilitated by an alignment mechanism for optimum positioning between an optical fiber 20 and clamps 262, 264 of a fiber tensioning apparatus. Optimum alignment does not necessarily require attachment of the indexing unit to a fiber tensioning apparatus 260.

Clamps 262, 264 attached at each end of the central load-free fiber portion 20 retain the central portion in its load-free condition, before subjecting the optical fiber to a selected tension force. The clamps comprise components of a fiber Bragg grating tensioning holder 266 used to stretch the fiber 20 under a prescribed load during fiber Bragg grating writing. A tensioning holder 266 according to the present invention comprises a voice coil 268 as a load applicator to a load cell 270 that measures the load applied between the pair of clamps 262, 264 holding the central portion of the fiber 20. After precise application of a desired selected tension, a pair of grippers 272, 274 isolates a measured fiber portion 276, between the clamps 262, 264, setting up a tension zone independent of outside tension variations. This maintains a prescribed load on the measured fiber portion 276 and prevents any fiber slippage relative to the grippers 272, 274 and hence the clamps 262,264. The fiber Bragg grating may be written into the bare portion 250, of the isolated, measured fiber portion 276 held between the pair of grippers 272, 274. Tension applied to a clamped optical fiber 20 anticipates shrinkage that will occur, changing the separation between grating features after a grating has been written and after a piece of axially strained measured fiber portion 276 has been released from the pair of grippers 272,274.

A voice coil driven tensioning holder 266 is favored over any of several possible load applying units including a DC servo motor and encoder combination, a precision pneumatic cylinder, a high precision micro-positioning linear stepper motor and a mechanical balance beam. A precision pneumatic cylinder, for example, provides insufficient fiber tension and fine pressure control to accurately apply a prescribed amount of tension to an optical fiber. A high precision micro-positioning linear stepper motor is equally incapable of providing required precise tension adjustment. Problems associated with the use of a mechanical balance beam include the fact that it is primarily a manual process not particularly conducive to automation.

Voice coil activated clamping structures are known. For example, U.S. Pat. No. 4,653,681 describes a voice coil activated fine wire clamp, used in wire bonding applications. Clamp jaws may be moved to an open position from a normally closed position using a voice coil motor under microprocessor control. A voice coil programmable wire tensioner, described in U.S. Pat. No. 5,114,066 also facilitates wire bonding. This shows that it's known to use a voice coil in wire bonding applications. However, it appears that the use of a computer controlled, voice coil motor has not been used to apply repeatable, precise amounts of tension to optical fibers for consistent production of optical fiber Bragg gratings having essentially the same wavelength response.

The advantageous use of a voice coil actuator 268 provides a linear output force corresponding to an input current that may be finely controlled. A high precision power supply with a voice coil actuator 268 produces a stable signal leading to an output force that is remarkably constant. This allows selection of a wide range of output force, limited only by the magnitude of energy transfer between a coil and a magnet. The output force of the actuator 268 is proportional to the input current, similar to a DC motor. A tensioning method based upon a voice coil actuator 268 occurs in response to bearing-free passage of energy between a coil and a magnet. Tension adjustment using this method offers significant advantages over prior methods that used addition and removal of static weights to increase or decrease tension on a fiber.

FIG. 23 shows that the mounts 278, 280 for the voice coil and load cell include air bushing carriages 282, 284 for minimal friction relative to a support bar 286. Air bushing carriages 282, 284 reduce static friction in the system to a low, almost insignificant level. Reduction of friction in the bushings 282, 284 allows accurate application of fiber tension corresponding to the force acting on the load cell 270. This results in improved control of the force generated by the voice coil actuator 268 and more consistent application of tension to an optical fiber 20. Each carriage 282, 284 includes a clamp 262, 264 for attachment to a central portion of an optical fiber 20. The separation between the clamps 262, 264 identifies the central portion of the optical fiber 20 to be tensioned. An extending guide rod 288 attached to the moving coil of the voice coil actuator 268 pushes against the load cell 270 increasing separation between the two carriages 282, 284. Increasing separation between the carriages 282, 284 operates through the clamps 262,264 to move them away from each other to add strain to the optical fiber 20. Upon attainment of a desired strain a pair of grippers 272, 274 grasp an inner measured fiber portion 276 of the optical fiber 20. The measured fiber portion 276 is somewhat shorter than the central portion between the clamps 262, 264. Accurate maintenance of force at selected levels allows the writing of acceptable fiber Bragg gratings. Force selection and control relates to the use of a high precision load cell 270 to measure and display the tension initially applied to the fiber 20 and maintained during the writing process. The load cell 270 may also provide feedback during computer controlled automated fiber Bragg grating writing.

An important aspect of writing a fiber grating is the need to hold a measured fiber portion 276 in a fixed, immobile condition throughout the process. This requires the use of a jaw assembly 290 attached particularly to the grippers 272, 274 for removably securing a measured fiber portion 276 in the desired immobilized condition. Clamps 262, 264 attached to the filament tensioning apparatus 260 may use the same jaw assembly 290 or another providing adequate clamping of a central portion of a fiber 20.

Figure 24:
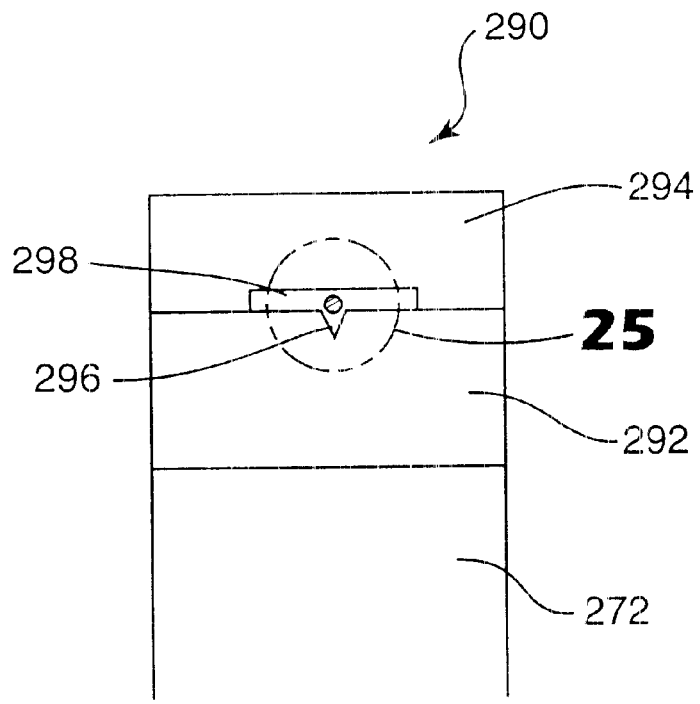
FIG. 24 provides a cross sectional view of a jaw used to prevent movement of a portion of an optical fiber while it undergoes modification.

FIG. 24 illustrates a fiber portion gripper 272 with an attached jaw assembly 290 of suitable design. The jaw assembly 290 comprises a lower jaw 292 attached at the end of a gripper 272 and an upper jaw 294 for engagement with the lower jaw 292 to grip and immobilize a measured fiber portion 276, shown in cross section in FIG. 24.

Figure 25:
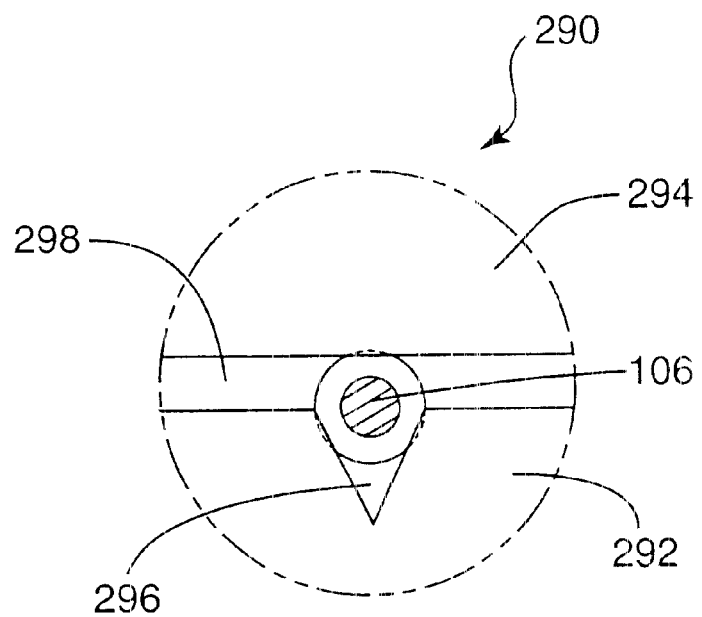
FIG. 25 is a detailed cross sectional view of the structure of the jaw shown in FIG. 24.

FIG. 25 provides a detail drawing of a V-shaped channel 296 formed in the upper surface of the lower jaw 292 and a rectangular cross section groove 298 in the lower surface of the upper jaw 294. The sizing of each of the channel 296 and groove 298 of the jaw assembly 290 corresponds to the diameter of the measured fiber portion 276 that is held in an immobilized condition.

A jaw assembly 290 design requires matching of the dimensions of a fiber 20 with those of a V-shaped channel 296 and a rectangular groove 298. Dimensional matching allows the application of substantially equal pressure at contact points around the circumference of a measured fiber portion 276 held immobile for the writing of a Bragg grating according to the present invention. Preferably a fiber 20 is held between the V-shaped channel 296 and the rectangular groove 298 with equal pressure applied at points of contact around its circumference. This is indicated in FIG. 25 by the fact that the two points of contact of the fiber 20 with the V-shaped channel 296 and the fiber's point of contact with the groove 298 are equidistant from the bare optical fiber 106. Uniform application of pressure leads to even distribution of stresses across the diameter of a measured fiber portion 276 to reduce fiber damage to a minimum, considering the amount of pressure required for the grippers 272, 274 to hold the measured fiber portion 276 in an immobile condition. V-groove chucks are known for clamping portions of optical fibers, as taught by U.S. Pat. Nos. 4,623,156 and 5,340,371. It does not appear in either case that consideration is given to equalizing the amount of pressure applied to points around the circumference of a fiber.

Figure 26:
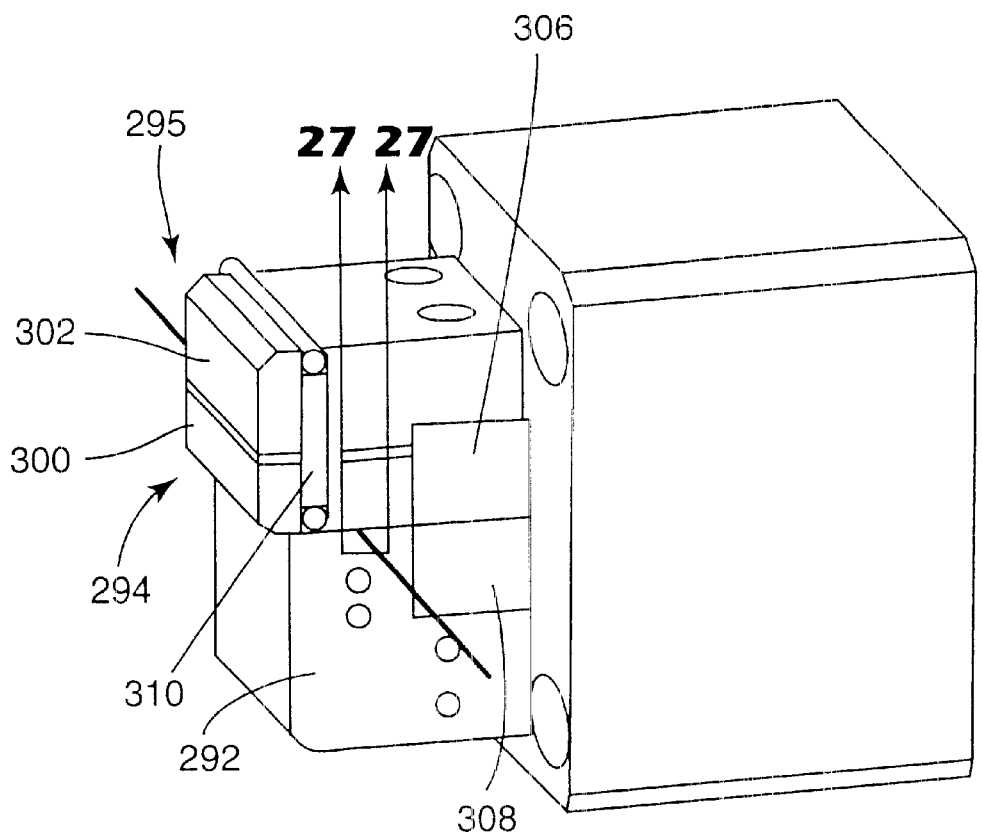
FIG. 26 is a perspective view of a jaw assembly according to the present invention.

In a preferred embodiment of the present invention, pressure equalization around the circumference of an optical fiber 20 requires the use of a floating upper jaw assembly 295, as shown in FIG. 26. The self-adjusting, floating upper jaw assembly 295 comprises a fiber clasp 300, a support flange 302, and an angular compensator 304 (see FIG. 27) separating the fiber clasp 300 from the support flange 302. A fiber clasp 300 may also be referred to herein as a filament clasp. Each gripper 272, 274 includes, in this case, an upper jaw mount 306 and a lower jaw mount 308. A lower jaw 292 attaches to the lower jaw mount 308 and an upper jaw assembly 295 attaches to the upper jaw mount 306 by the support flange 302. Suspension of a fiber clasp 300 from a support flange 302 preferably uses a spring-loaded connector 310. Spring tension operating between the fiber clasp 300 and support flange 302 retains an angular compensator 304 between them. During capture of a filament 20 between the lower jaw 292 and upper jaw 294 of a gripper 272, 274, the use of a floating upper jaw assembly 295 allows application of gripping force to a filament 20 substantially without displacement or rotation of the filament 20. The clamps 262, 264 may also include a floating jaw assembly.

Figure 27:
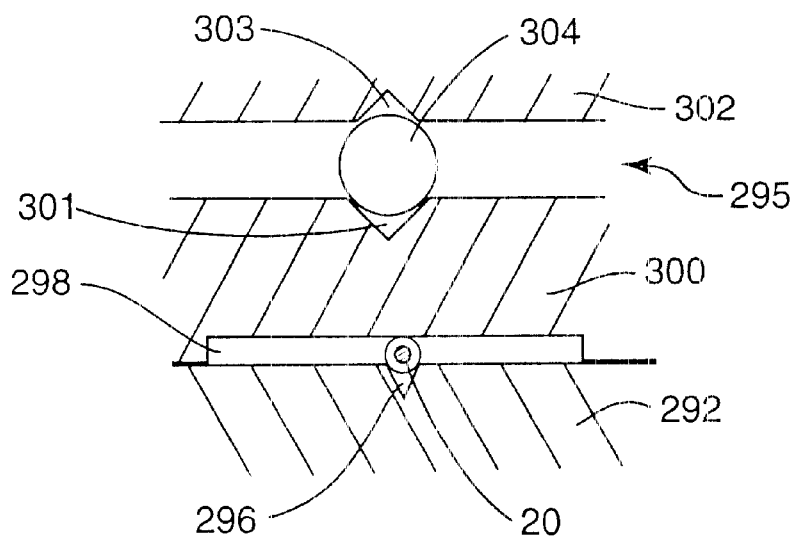
FIG. 27 is a cross section taken through line 27—27 of FIG. 26.

FIG. 27 shows the result of gripping a filament 20 between a floating jaw assembly 295 and a lower jaw 292. As the floating jaw assembly 295 moves towards the lower jaw 292, the rectangular groove 298 of the filament gripper 292, 294 makes contact with a filament positioned in the V-shaped channel 296 of the lower jaw 292. As contact occurs, the filament clasp 300 may adjust slightly to apply gripping force uniformly to the filament 20, without disturbing it. Adjustment of the filament clasp 300 relies upon its independent movement due to the angular compensator 304 that separates it from the support flange 302. A preferred angular compensator 304 according to the present invention comprises a spherical element that prevents contact between the filament clasp 300 and the support flange 302. Preferably the angular compensator 304 seats between a substantially conical shaped depressed portion 301 in the fiber clasp 300 and a substantially conical recess 303 in the support flange 302. The angular compensator 304 maintains separation of the support flange 302 from the filament clasp 300 to allow them to move independently. Also, the spherical structure of the angular compensator 304 allows effective change of angle around the perimeter of the filament clasp 300.

The previous discussion provided a description of positioning, clamping and gripping a single optical fiber 20 using an apparatus 260 including a tensioning holder 266 to tension the fiber 20 during writing of a Bragg grating. The description involves the relative positioning between a filament organizer 10 and a tensioning holder 266. When a filament organizer 10 represents one of a number of organizers 10 in a stacked configuration 68 the writing of a Bragg grating may be accomplished in a variety of ways. For example, fiber optic Bragg gratings may be written one at a time using a step and repeat process to move a fiber 20 carried in a selected filament organizer 10 into the correct position, relative to the tensioning holder 266 to execute writing of a Bragg grating. The wavelength response of an optical fiber 20 may be monitored, as described previously, during Bragg grating writing. An alternative to sequential writing of Bragg gratings may be to use a bank of tensioning holders 266 and related writing devices for producing a plurality of Bragg gratings simultaneously.

The step and repeat process using an indexer to reposition a stacked configuration 68, e.g. preferably by up or down directional movement, presents a new fiber to the Bragg grating writing device. The stacked configuration 68 fits into the platform of an indexer adapted to provide mating with a known positional relationship between a stacked configuration 68 and the platform using alignment between the spacer blocks 70 and organizer mounts 72. Having established the preferred placement of the stacked configuration 68 relative to the indexer, and having made connection of the fiber pigtails 252 to the optical detection system, a scan of each fiber verifies the existence of reliable optical connections.

The placement of a stacked configuration 68 in an indexer with fiber optic connection to an optical detection system precedes seriate Bragg grating writing process in which the indexer initially uses an optical sensor to scan the filament organizers 10, counting the number in the stacked configuration 68. This process designates the first filament organizer 10 in the stacked configuration 68. A sequence of operations modifies the optical fiber 20 held in this first filament organizer 10. Before modifying the optical fiber itself, removal of the effect of the constant force tensioner 58, as described previously, uses a force reduction assembly comprising a pair of pulleys 64 on either side of a notch 66 formed in an edge of the support board 12. The tension wire 62, passing around the pulleys 64 and across the notch 66, may be grasped in the vicinity of the notch 66 and extended slightly, parallel to the edge of the board 12, and toward the nearest guide 24. This releases the tension on the rotary spool 18 of the filament organizer 10, thereby releasing the tension in the filament or optical fiber 20.

Preparation for modifying a filament 20, in the form of an optical fiber, requires securing the tension-free portion of the optical fiber using an apparatus that combines a filament tensioning apparatus 260 and an interference pattern generator (not shown). Each of the filament tensioning apparatus 260 and the interference pattern generator may be moved separately initially to secure and position an optical fiber 20, as discussed previously, and then to modify the fiber's structure.

The filament tensioning apparatus 260 grips the fiber 20, as described above, using a first clamp 262 and second clamp 264. Force operating between the two clamps 262, 264 applies tension to the portion of optical fiber 20 between them. The force may be generated using a voice coil actuator 268. The amount of tension is predetermined and measured using a load cell 270. At this point the optical detection system provides a reference scan of the optical fiber 20, including the portion held under tension between the clamps 262, 264.

To reproducibly modify an optical fiber 20, preferably a measured portion 276 of the fiber 20 remains in a fixed condition held by a first gripper 272 and second gripper 274 that grip the fiber and hold it. Once the measured portion 276 of the optical fiber has been immobilized, an interference pattern generator moves into close proximity to the measured portion 276 of the optical fiber 20. Light, from a contained laser source, passes through an opened shutter, and an optical system, including the interference pattern generator to produce an interference pattern. The proximity of the interference pattern generator to the optical fiber 20 provides sufficient energy to reproduce the line characteristics of the interference pattern or interferogram in the core 106 of the optical fiber 20, preferably within the measured fiber portion 276. Impingement of actinic radiation, produced by an ultraviolet laser, produces an optical fiber Bragg grating as a result of changes in refractive index in parts of the optical fiber core 106 affected by the radiation. Refractive index modulation corresponds to the pattern of the interferogram, produced by the interference pattern generator. Progress in reproduction of an interferogram in the core of an optical fiber may be monitored using an optical detection system for data acquisition. Data acquisition follows changes in the transmission spectrum produced by a developing Bragg grating with time. Upon sensing the desired transmission spectrum, the optical detection system closes the shutter to prevent further exposure of the optical fiber to laser light.

Following completion of optical fiber modification and removal of the interference pattern generator from the vicinity of the measured fiber portion, the grippers 272, 274 and clamps 262, 264 retract from the fiber 20 to allow the filament tensioning apparatus to move to the next filament organizer 10 in the stacked configuration 68. Once separation of filament organizer 10 from the Bragg grating writing equipment occurs, the force reduction assembly releases the optical fiber placing it once again under the tension generated by the tensioner 58 of the filament organizer 10. This completes the modification of a given optical fiber so that the indexer can readjust to align the optical fiber 20 in the next filament organizer 10, in a stacked configuration 68, with the filament tensioning apparatus and the interference pattern generator before repetition of the Bragg grating writing cycle.

Annealing using an annealing oven at 300° C. for 10 minutes provides stabilization for a Bragg grating produced by refractive index alteration of an optical fiber. An annealed Bragg grating may require protection by recoating the central portion of the optical fiber, which was previously stripped of protective coating. Any of a number of methods may be used for protective recoating of optical fiber Bragg gratings including in-mold application, extrusion coating and spray coating a fiber with a curable liquid coating. Equipment is commercially available for in-mold application of liquid recoat formulations. The quality of in-mold optical fiber section recoating varies with the skill of an operator to carefully position a fiber in a mold cavity. Also, product yields have been reduced because of coating defects and fiber strength issues associated with fiber handling and sectional recoating. As alternatives, either spray coating or extrusion coating may be used for recoating optical fibers that include Bragg gratings according to the present invention.

A filament organizer 10 according to the present invention may be used to advantage for positioning uncoated portions 250 of and optical fiber 20 in a fiber recoating mold. Since the filament organizer 10 also applies tension to the optical fiber 20, an alignment plate attached to a mold recoater of the type supplied by Vytran Corporation of Morganville, N.J. is the only requirement for correct fiber positioning within a groove such as a semicircular or V-groove of the split mold apparatus. The alignment plate may use strategically positioned studs to engage the through holes 80 of the planar support 12 of a filament organizer 10. This eliminates the need for mold positioning using micromanipulator platforms and the like. The effective diameter of the groove is somewhat greater than that of the remaining coated portions of the fiber. Due to pre-tensioning of the fiber by the filament organizer the common need for external tensioning is eliminated. Once the vulnerable uncoated portions 250 of the fiber 20 have been suspended clear of the groove surface, the hinged mold is closed and recoating material is injected into the groove until it extends to the coated portion of the fiber. The molding material is then cured yielding a recoated section with dimensional characteristics essentially identical to those of the original coated fiber.

Fiber recoaters of the type described briefly above include a split steel mold, each portion of which contains a matching semicircular groove to accommodate the fiber. The grooves, when clamped together, formed a cylindrical bore slightly larger than the coated fiber OD to permit escape of air during injection of the coating material. The original coating in this arrangement keeps the uncoated section suspended in the bore. A short uncoated length of fiber, typically no more than half an inch, minimizes the possibility of damage through contact with the bore. Also, a series of clamps, attached on either side of a central fiber portion, prevent the uncoated portion from touching the bore. Before injecting recoating fluid, the upper half of the mold is clamped in position to form the cylindrical bore. The curable recoating fluid may be a room temperature curing epoxy resin or other resin that cures either at elevated temperature or in response to suitable radiant energy such as ultraviolet radiation.

Figure 28:
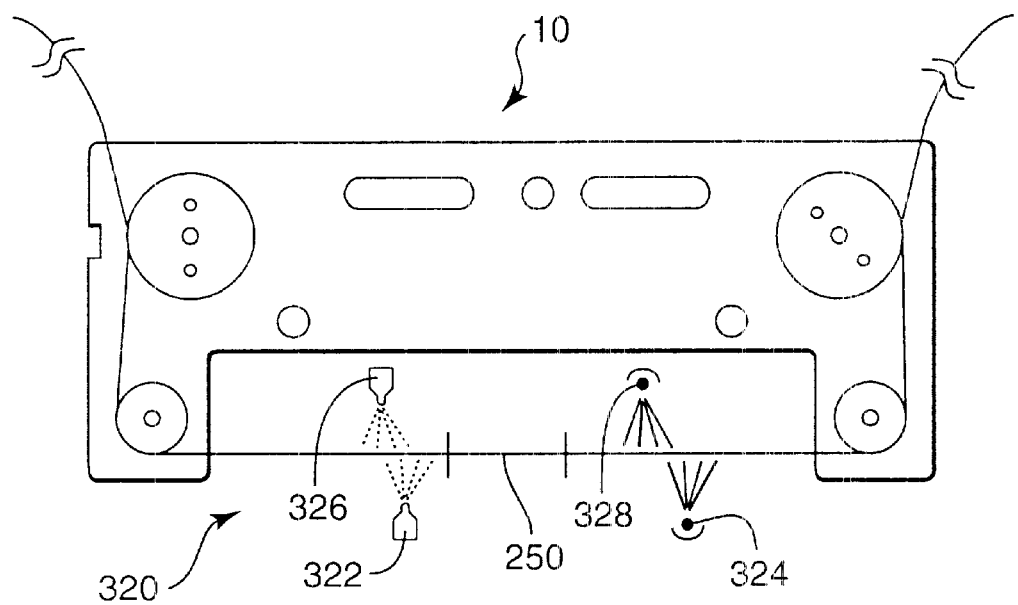
FIG. 28 is a diagrammatic side elevation of a filament organizer according to the present invention positioned in a spray recoating apparatus.

FIG. 28 illustrates the use of a filament organizer 10 to store an optical fiber 20 having a bare portion 250 that has been modified to include a Bragg grating. An exposed Bragg grating may be recoated after positioning the filament organizer 10 in a suitable spray recoating apparatus 320. For correct positioning of a filament organizer relative to a spray recoating apparatus 320 the bare portion of an optical fiber 250 lies in the path of spray ejected from a recoating spray head 322. Such correct positioning is achievable by any of a variety of methods and devices. One such method uses a plate suitably positioned relative to a spray recoating apparatus and including alignment studs to engage through holes in a filament organizer 10 to place the bare portion 250 of an optical fiber 20 in the optimum position for application of recoating spray.

A spray recoating apparatus 320 comprises at least one recoating spray head 322 and a radiation source 324. A filament organizer 10 is adapted for oscillatory movement of the bare portion 250 of an optical fiber between the recoating spray head 322 and the radiation source 324. Preferably, the position of the recoating spray head 322 is from about 1 cm to about 2 cm from the fiber 20, preventing contact between the spray head 322 and a deposited coating. The spray recoating method provides controlled sectional recoat that achieves performance characteristics not obtainable from conventional in-mold recoating processes. It is a non-contact method since the optical fiber 20, including the bare portion 250, does not touch any part of the recoating equipment. This represents another benefit of suspending a fiber 20 in a filament organizer 10 that may be readily attached to the recoating apparatus with precise fiber 20 to spray head 322 alignment. Another benefit of spray recoating involves over coating one recoating composition with another exhibiting different properties to produce a multilayer buffer structure, around a fiber, including layers that differ in properties such as modulus and durability or hardness.

The use of a spray recoating process allows flexible placement of a single filament or multiple filaments in the path of spray or mist from a recoating spray head 322. Where a filament organizer 10 provides the preferred means for handling an optical fiber 20, several filament organizers 10 may be closely located with variable orientation to place a plurality of fibers in the path of a single spray or directed mist. An additional advantage of spray recoating versus conventional cavity-mold recoating is the provision of a recoating spray head 322 that may be adjusted or translated to differing lengths of bared optical fiber portions 250.

As the bared portion 250 of a fiber 20 traverses the location of the recoating spray head 322, one side of the bare fiber portion 250 receives a light deposit of droplets from a mist of a curable recoating composition. Movement of the filament organizer then places the deposit of droplets in the illumination path of the radiation source 324. The radiation cures the layer of recoating composition. Returning to the location of the recoating spray head 322, the filament organizer 10 flips over to expose the opposite side of the previously bare fiber portion 250 to the spray of curable recoating composition. This allows application of a fine mist of recoating composition to the exposed optical fiber surface. This layer may be cured as described previously. Repeated processing by coating and curing with oscillation and flipping of the filament organizer 10 protects the fiber with multiple layers of recoating composition. The recoated fiber surface has a matte appearance resulting from the build up of successive layers of coating material. Coating topography up to about 15 μm was revealed on the surface of a microscope slide by surface scanning with an ELFA STEP mechanical stylus profilometer available from Tencor Corporation.

Approximately fifty applications of recoating composition followed by curing, after each pass, provide a layer having a thickness over the recoated length similar to that of the original buffer coatings on other parts of an optical fiber 20. This technique allows layers of recoating composition to be applied to the surface of an optical fiber to build a protective recoat having a thickness of from about 10 microns to about 100 microns on a bare fiber 106. The diameters of spray-recoated optical fibers may be measured using a microscope and a QUADRA-CHEK 2000, from Metronics Inc., Bedford, N.H. Coating thickness may be varied depending on the application.

Another embodiment of the present invention provides a second recoating spray head 326 and optionally a second radiation source 328 positioned opposite the previously discussed recoating spray head 322 and radiation source 324. The description of multiple spray heads 326 and radiation sources 328 as occupying opposing or staggered opposing positions includes alignment of positions but is not limited thereto. Any number of spray heads, positioned strategically, may be used in a fiber recoating process. Placement of a spray head and radiation source on both sides of an optical fiber 20 facilitates recoating of both sides of the bare fiber portion 250, while eliminating the need to flip the filament organizer through 180°. As indicated previously, the use of additional radiation sources 328 is optional since the beam from a single radiation source 328 may be directed to effect curing around the circumference of a recoated fiber.

The contours of a deposit of droplets applied to a bare fiber 106 will reflect the size and shape of the droplet cloud issuing from a spray head 322. If required, a means for shaping the droplet cloud could produce a desired pattern of droplets on the surface of a fiber 20. Suitable shaping means include stencils, other types of masking devices, and stream deflectors such as air knives.

A preferred recoating process according to the present invention uses an air knife to direct an atomized stream at various angles of contact with an optical fiber 20. Air knife adjustment of the shape of a droplet cloud, and its angle of impingement with an optical fiber 20, may allow the use of a minimum of spray heads 322, 326 to achieve optimum fiber recoat uniformity and concentricity. Also, the use of air knife deflection of small volumes of recoating compositions provides an advantage when compared to the control of diverging streams of relatively high volume spray heads described in Japanese patent JP 60-122754. U.S. Pat. No. 5,219,120 teaches the use of an air horn that provides a moving sheet of air to entrain a substantially uniform linear dispersion of atomized fluid moving above and extending substantially across the width of the air horn. The air horn spreads the dispersion of atomized fluid to a width suitable for spraying the flat surface of a circuit board. Such extensive spreading of a cloud of droplets does not apply directly to narrow curved surfaces such as those of an optical fiber. Also, the air horn described in U.S. Pat. No. 5,219,120 is a separate structure from the fluid atomizer.

Preferably air knife deflection according to the present invention occurs through the use of an air knife attachment that fits over the exit nozzle of a spray head. The air knife attachment includes a pair of receiving chambers, at least one on either side of the spray head, into which air may be directed. Each receiving chamber has an air entry at one end connected to an air reservoir. The opposite end of each chamber includes an air knife slit that exits from the chamber at an angle to the axis of the spray head. Air issuing from an air knife slit deflects the spray cloud, generated e.g. by an ultrasonic atomizing spray head, at an angle corresponding to the angle formed between the slit and the axis of the spray head. Independent operation of each air knife, described above, causes selective deflection of a spray cloud at an angle that directs the droplet cloud towards an uncoated portion of an optical fiber. Selective deflection of a droplet cloud allows positioning of a number of optical fibers around a spray head nozzle. Impingement of air from exit slots of air receiving chambers deflects atomized spray at various angles for sequential recoating of the number of optical fibers held around the spray head using filament organizers 10 according to the present invention. The use of air deflection preferably requires that the recoating composition is not oxygen inhibited. This does not prevent the use of oxygen inhibited recoating fluids providing an inert gas is connected to the receiving chambers of the air knife attachment.

The process of recoating a bared portion 250 of an optical fiber 20 may use spray heads 322, 326 based upon either ink jet or ultrasonic atomization technology. Preferably, the application of curable recoating composition, to an optical fiber 20, uses ultrasonic atomization technology to dispense small particles (<50 μm) of a fluid, having a viscosity from about 40 to about 900 centipoises, preferably 40 centipoises to about 400 centipoises, over a bared portion 250 of the fiber 20. Viscosity measurements were made at 25° C., using a BOHLIN CS-50 rheometer. Other requirements for a coating composition for recoating optical fibers according to the present invention depend upon the intended use of a recoated optical fiber device, such as a Bragg grating. Example 1 of Table 1 provides a load bearing coating, preferably having a high modulus, high glass transition temperature (Tg), and temperature stability above the upper operating temperature for a selected application. Examples 2 and 3 produce cured coatings that flex and bend with a recoated portion of a fiber. Preferably coating compositions, in this case, possess thermomechanical properties similar to undisturbed buffer coating, originally applied to the fiber. Immediate curing of such a coating reduces undesirable agglomeration, which could result in beading or poor concentricity.

An ultrasonic atomization processes differs from a spray atomization process that, requires air velocity to break up a sprayable composition into droplets. Droplet size of a spray atomization process is larger (50 to 100 microns diameter) and the spray velocity, at its lowest pressure of ~20 psi, propels the droplets with a force causing the droplets to spread upon impact with a fiber surface. Being relatively high, the impact force of an air atomized spray against a fiber causes build-up of agglomerated droplet beads accompanied by formation of a non-concentric coating.

The ultrasonic atomization process generates volumes of coating composition that are extremely small, in the range from about 0.001 ml/min to about 0.010 ml/min using a 2.0 cc glass syringe available from Popper & Sons. The flow rate for dispensing a substantially non-directional cloud of droplets less than 50 microns in diameter depends upon the speed at which the fiber is scanned in front of the atomizer head. A low velocity flow of nitrogen, or other inert carrying gas directs the cloud of ultrafine droplets of recoating composition towards a target surface. The low cloud volume and extremely small droplet size cause the formation of a textured discontinuous covering of the fiber surface. Although coatings are low enough in viscosity for spray application, preferred coating compositions exhibit minimal flow, after application, prior to coating. Flow and droplet agglomeration is further limited because the recoating composition, immediately after application, undergoes exposure to curing radiation from the radiation source 324, 328. Repeated application of recoating composition builds up a protective coating over a bared optical fiber portion 250. A recoated optical fiber preferably has a relatively smooth appearance bubble-free appearance. This requirement guides the selection of materials used to prepare recoating compositions according to the present invention.

Suitable recoating compositions include low molecular weight, low viscosity epoxy functional, 100% solids resins that photocrosslink preferably via an ionic mechanism initiated by a cationic photoinitiator, especially an iodonium salt photoinitiator. Such coatings have good adhesion to the unstripped buffer coats on a fiber as well as to the bare surface of the fiber. Ionic curing occurs without exclusion of oxygen. Radical curing recoating compositions may also be used in an inert environment. Suitable radiation sources for photocrosslinking include those having wavelength emission in the blue/visible and ultraviolet wavelength regions of the spectrum. Cured coatings according to the present invention A typical cured recoating composition has an elongation at least equal to and preferably greater than that of glass, i.e. more than 7%. Also, a cured recoating composition has toughness and sufficient adhesion to glass to withstand accidental rubbing or contact with other objects during handling of a recoated fiber.

TABLE 1

Filament Coating Formulations

| Material* | Example 1 | Example 2 | Example 3 |
|---|---|---|---|
| Weight % Epoxy A | 57.0 | — | — |
| Weight % Epoxy B | 38.0 | — | — |
| Weight % Epoxy C | — | 67.0 | 66.5 |
| Weight % Epoxy D | — | 25.1 | 28.5 |
| Weight % Polyether Glycol | — | 2.9 | — |
| Weight % Iodonium Salt Solution | 5.0 | 5.0 | 5.0 |

*Key:
Epoxy A is CYRACURE UVR-6105 available from Union Carbide Corporation.
Epoxy B is HELOXY 107 available from Resolution Performance Products.
Epoxy C is EPONEX 1510 available from Resolution Performance Products.
Epoxy D is HELOXY 7 available from Resolution Performance Products.
Polyether Glycol is TERATHANE 650 available from E. I. du Pont de Nemours and Company.
Iodonium salt solution is UV 9380C available from General Electric Company.

Measurement of Coating Composition Viscosity

A Bohlin Model CS-50 controlled stress rheometer was used to measure the viscosities of coating compositions, for recoating filaments according to the present invention. The test method uses parallel plate geometry and "stress viscometry" mode. Viscosity measurement begins with placement of a coating composition on the base surface of the parallel plate geometry. A second surface, mounted to rotate on a spindle, is lowered into contact with the coating composition until a specified gap exists between the surfaces of the parallel plate geometry. Rotation of the spindle raises the rate of rotation to a number of revolutions per minute to produce a predefined stress (torque). The calculation of viscosity values includes consideration of the geometry of the surfaces, the torque and the gap. Viscosities cited herein were obtained at 25° C. using a surface diameter of 20 mm, a gap between surfaces of 0.3 mm, and a stress of 93.8 Pascals.

A spray head that included an ultrasonic atomizer was used to apply curable recoating formulations, shown in Table 1, to the bare surfaces of several samples of silica fiber, each having a diameter of about 125 microns. Each formulation was dispensed via the tip of the atomizing horn of an ultrasonic atomizer available from Sono-Tek. The power supply of the ultrasonic atomizer was set to a level of 5.4 watts. Successful atomization of recoating formulations, having viscosities in the range from about 40 centipoises to about 400 centipoises was achieved using a micro-bore fluid delivery tube through the center of the nozzle body of the ultrasonic atomizer. Most preferably the coating composition has a viscosity of about 200 centipoises. Recoating formulations were supplied to the micro-bore tube at a syringe pump delivery rate of 0.015 ml/min. A preferred method uses a 21.5 gauge micro-bore tube available from Small Parts Inc., Miami, Fla. This provides precise control of small volumes of recoating composition delivered to the point of atomization.

Ultrasonic atomization as described previously produces a non-directional mist of coating composition that needs to be entrained in a directional gas stream. Preferably the directional gas stream comprises an inert gas, e.g. nitrogen gas, under the control of a shroud around the micro-bore tube. A nitrogen gas stream flowing through the shroud around the atomizer head at a rate of 1.0 liter/min yields a suitably controlled atomized mist of recoating formulation. Adjustment of the air shroud alters the contours of the gas stream thereby modifying the size, shape and coverage of a stream of droplets of curable recoating formulation impinging on a selected surface. A continuous coating may be formed on a surface using as few as about 4 to about 6 applications of a coating formulation. However, depending upon process conditions, application of coating formulation may need to be repeated form about 40 to about 60 times to build a coating thickness of up to 250 microns on a selected surface.

A filament recoating formulation was shown to produce a suitable stream of material for application using an ink jet printing/spray head as follows:

EXAMPLE 4

| Epoxy A | 76.0 weight % |
|---|---|
| Epoxy B | 19.0 weight % |
| Photoinitiator solution | 5.0 weight % |

The photoinitiator solution contains 40 parts or iodonium methide, 60 parts of decyl alcohol and 4 parts of isopropylthioxanthone.

The ink jet printing/spray head operated at a head temperature of 70° C. A ink jet printing/spray head, available from Trident International Inc., Brookfield, Conn. was selected to apply recoating composition to several samples of silica fiber, each having a diameter of 125 microns. The print head has 64 nozzles, each 50 microns in diameter. Use of a filament organizer mounted on a filament recoating apparatus provided suitable alignment of a fiber with an ink jet printing/spray head prior to application of recoating composition. Particles of the composition were jetted over a 1 cm length, on one side of a filament of each of five samples of silica fiber. An EFOS ULTRACURE radiation source (EFOS Inc., of Mississauga, Ontario, Canada), with an ultraviolet radiation wand, was used to direct energy to the coated sample to initiate cure. Repeated passes under the recoating spray head, followed by ultraviolet radiation curing, produced adequate coverage of the bare optical fiber.

Figure 29:
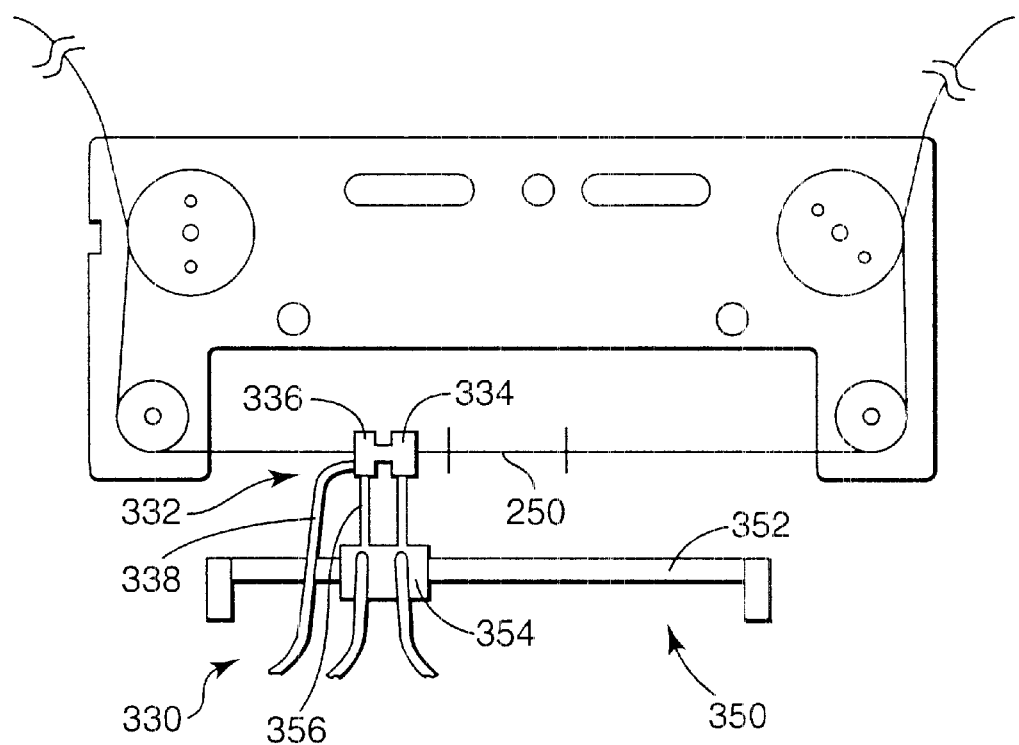
FIG. 29 is a diagrammatic side elevation of a filament organizer according to the present invention positioned in a split die recoating apparatus.

FIG. 29 provides a diagrammatic representation of a preferred split die extrusion coating method that uses an recoating fluid extrusion apparatus 330 having a die head assembly 332 encircling an optical fiber 20 to recoat a bared optical fiber portion 250 that contains a Bragg grating. A study, reported in Electronics Letters Vol. 34, No. 12, Jun. 11, 1998, investigated a split die recoating process to apply a solution of polyimide to a bare portion of an optical fiber. The process involved drawing a fiber through the fluid filled split die, then driving off solvent at 70° C. followed by baking the polyimide recoated section at 300° C.

Split die extrusion coating according to the present invention offers improvements for fiber recoating including controlled application and relatively low temperature curing of recoating compositions as follows. The die head assembly mentioned above comprises a split sizing die 334 and an in-line radiation cure chamber 336 that is closed around the optical fiber 20. Accurate fiber 20 positioning, for recoating and protection of the Bragg grating occurs during engagement of a filament organizer 10 with the recoating fluid extrusion apparatus 330. Any one of a variety of methods may be used for engagement between a filament organizer 10 and an extrusion apparatus 330 provided that the die head assembly 332 has movable alignment to deposit a substantially uniform layer around the fiber portion 250 that needs recoating. During recoating, the bared fiber portion 250 of an optical fiber 20 remains stationary between fiber positioners. The split sizing die 334 lies adjacent to one end of the bare fiber portion 250 from which curable recoating composition will be applied across the remainder of the bare portion 250. Photocurable coatings extrude from the leading edge of the sizing die 334 as it traverses the length of the bared optical fiber portion 250. The radiation cure chamber 336 moves with the sizing die 334 following behind it to initiate curing of the photocurable recoating composition immediately after its deposition on the surface of the optical fiber 20. The recoating composition curing reaction preferably requires an inert atmosphere. For this purpose an inert gas delivery tube 338 directs a flow of nitrogen into the radiation cure chamber 336 that is illuminated using a suitable source of radiation, preferably ultraviolet radiation.

A linear transport mechanism 350 adjacent to the coating head 332 includes a guide rod 352 and a carriage 354 slidably mounted on the guide rod 352 for movement along the guide rod 352. A connecting rod 356 from the carriage 354 to the coating head 332 provides linear displacement of the coating head assembly 332 during movement of the carriage 354 to move the coating head 332 from the first boundary to the second boundary of a bare portion 250 of an optical fiber 20. Curable fluid may be extruded from the sizing die 334 and energy from the radiation source 336 used to cure the fluid during recoating of the bare portion 250 of an optical fiber 20.

During its motion, the split die 334 applies a substantially uniform thickness of recoating composition along a length of fiber 20 that includes the bare fiber portion 250 and margins at each end that overlap the original secondary buffer 102. Uniform coverage of an optical fiber 20 with a concentric layer of a recoating composition relies upon the accuracy of positioning a filament organizer 10 to preferably place the fiber 20 coaxial with the sizing die 334. The radiation cure chamber 336 has a size such that its internal surfaces do not touch the layer of recoating composition, either before or after curing. When coating concentrically, the bare fiber portion 250 will only come into contact with the recoating composition. The split configuration of the sizing die 334 and the radiation cure chamber 336 allows easy positioning of a fiber 20 in a recoating fluid extrusion apparatus 330. Correct fiber positioning, as mentioned previously, is a result of accurate engagement of a filament organizer 10 with a recoating fluid extrusion apparatus 330. Upon re-opening the die head assembly 332, after completing the recoating and curing process, a gap between a recoated fiber 20 and the internal surfaces of the radiation cure chamber 336 allows clean removal of the fiber 20 from the assembly 332.

Changes in the length of bared fiber portions 250 may be accommodated by adjustment of the distance that a die head assembly 332 may travel while extruding recoating composition. The surface tension of the recoating composition tends to smooth out any irregularities in the coating before it reaches the radiation cure chamber 336, even though the die head assembly 332 has a length of only about 6.0 mm to about 7.5 mm. A benefit of this short length is avoidance of contamination by recoating composition. Also small amounts of residual recoating composition may be relatively easily cleaned from inside the assembly 332.

Although a bare fiber portion 250 has a horizontal orientation during application of protective recoating composition, the moving extrusion die 334 produces similar results to coating heads operating vertically during fiber draw coating processes. The relative motion between the sizing die 334 and the fiber 20 simulates the draw process. This eliminates mold recoating defects such as flash, gate marks, sinks, and coating delamination caused by coating adhering to the surface of a mold.

The extrusion of terminal margins, at each end of the bare fiber portion 250, means that initial deposit of material by extrusion occurs at a region of the fiber 20 that is still protected by the original coating 100, 102. This substantially prevents optical fiber strength losses generally associated with loading the fiber 20 into a traditional recoating mold. Bared fiber portions 250 recoated by split die extrusion according to the present invention provided evidence of strength retention by surviving Vitran proof testing to levels exceeding 800 kpsi.

A process for manufacturing an optical fiber Bragg grating has been described to show how a compact filament organizer 10 may be used to handle and transport optical fibers 20 between various types of processing equipment. Each piece of processing equipment may include a pair of mounting pins for alignment and insertion in through holes 80 of a filament organizer 10 for correct positioning of a central portion of an optical fiber 02 relative to the selected piece of apparatus. Such easy positioning also facilitates automation of at least parts of the Bragg grating manufacturing process unlike previous similar processes that rely upon operator skill for correct fiber positioning. It will be appreciated that engagement between mounting pins and through holes is only one of a number of methods for aligning an optical fiber for processing.

As required, details of the present invention are disclosed herein; however, it is to be understood that the disclosed embodiments are merely exemplary. Therefore, specific structural and functional details disclosed herein are not to be interpreted as limiting, but merely as a basis for the claims and as a representative basis for teaching one skilled in the art to variously employ the present invention.

What is claimed is:

1. A filament tensioning apparatus comprising:
  a tensioning holder including:
    at least one support bar;
    a first carriage mounted at a first location on a said support bar said first carriage having a first clamp and a voice coil mounted thereon for movement relative to a said support bar;
    a second carriage mounted at a second location on a said support bar such that a separation exists between said first location and said second location said second carriage having a second clamp and a load cell mounted thereon for movement relative to a said support bar; and
    a guide bar extending from said voice coil for contact with said load cell to adjust said separation of said first location from said second location to apply tension to a filament held between said first clamp and said second clamp.

2. The filament tensioning apparatus of claim 1, further including a pair of grippers secured to said filament tensioning apparatus in axial alignment with said first clamp and said second clamp at a distance that is less than said separation of said first clamp from said second clamp, said grippers substantially immobilizing a measured filament portion held therebetween.

3. The filament tensioning apparatus of claim 1 wherein said first carriage and said second carriage each include a bushing for sliding engagement with said at least one support bar.

4. The filament tensioning apparatus of claim 3 wherein said bushing is an air bushing to provide substantially frictionless sliding engagement with said at least one support bar.

5. The filament tensioning apparatus of claim 1 further including a coupling for attaching a filament organizer to said filament tensioning apparatus to position a filament to be held between said first clamp and said second clamp, said filament organizer having an extended filament between a fixed spool and a rotary spool.

6. A filament tensioning apparatus for releasably securing an optical fiber, said tensioning apparatus comprising:
  a filament organizer having an optical fiber extending between a lockable spool and a rotary spool, said optical fiber including a measured fiber portion and a bare fiber portion;
  a tensioning holder including:
    a support bar;
    a first carriage movably mounted at a first location on said support bar said first carriage including an upper surface having a first clamp and a voice coil mounted thereon for movement relative to said support bar;
    a second carriage movably mounted at a second location on said support bar such that a separation exists between said first location and said second location said second carriage including an upper face having a second clamp and a load cell mounted thereon for movement relative to said support bar, said second clamp in axial alignment with said first clamp to secure said measured fiber portion including said bare portion thereof, located inside a first boundary and a second boundary, between said first clamp and said second clamp;
    a guide bar extending from said voice coil for contact with said load cell to adjust said separation of said first location from said second location, to change tension applied to said measured fiber portion, during activation of said voice coil; and
    a pair of grippers secured to said filament tensioning apparatus, and in axial alignment with said fist clamp and said second clamp to substantially immobilize said bare fiber portion.

7. The filament tensioning apparatus of claim 6 wherein said filament organizer further includes a support having a first surface opposite a second surface, said lockable spool and said rotary spool being adjacent to said first surface.

8. The filament tensioning apparatus of claim 6 wherein said first carriage and said second carriage each include a bushing for sliding engagement with said support bar.

9. The filament tensioning apparatus of claim 8 wherein said bushing is an air bushing to provide substantially frictionless sliding engagement with said support bar.

10. A method of filament tensioning comprising the steps of:
  providing a tensioning holder including at least one support bar;
  attaching a filament to a first clamp coupled to a first carriage mounted at a first location on a said support bar said first carriage having a voice coil mounted thereon for movement relative to a said support bar;
  holding the filament using a second clamp coupled to a second carriage mounted at a second location on a said support bar such that a separation exists between said first location and said second location said second carriage having a load cell mounted thereon for movement relative to a said support bar; and
  activating said voice coil to move a guide bar extending from said voice coil to contact said load cell to adjust said separation of said first location from said second location to apply tension to a filament held between said first clamp and said second clamp.

11. The method of claim 10 wherein said first carriage and said second carriage each include a bushing for sliding engagement with said at least one support bar.

12. The method of claim 11 wherein said bushing is an air bushing to provide substantially frictionless sliding engagement with said at least one support bar.

13. The method of claim 10 further including an attachment for positioning a filament organizer adjacent to said tensioning holder to position a filament to be held between said first clamp and said second clamp, said filament organizer having an extended filament between a fixed spool and a rotary spool.

* * * * *

UNITED STATES PATENT AND TRADEMARK OFFICE
CERTIFICATE OF CORRECTION

PATENT NO. : 6,665,483 B2
DATED : December 16, 2003
INVENTOR(S) : Gatica, Anthony W.

It is certified that error appears in the above-identified patent and that said Letters Patent is hereby corrected as shown below:

<u>Drawings,</u>
Sheet 12 of 15, Fig. 23, delete the reference numeral "228" and insert in place thereof -- 288 --.

<u>Column 1,</u>
Line 27, after "locations" insert -- . --.
Line 44, delete "World" and insert -- world --, therefor.
Line 54, after "link" insert -- . --.
Line 61, insert -- , -- before "an".

<u>Column 11,</u>
Line 36, delete "fist" and insert -- first --, therefor.

<u>Column 13,</u>
Line 50, after "view" insert -- . --.
Line 56, delete "an" and insert -- a --, therefor.

<u>Column 14,</u>
Line 4, after "transition" insert -- . --.

<u>Column 15,</u>
Line 5, delete "Theses" and insert -- These --, therefor.

<u>Column 16,</u>
Line 34, insert -- . -- before "The".

<u>Column 19,</u>
Lines 4 and 26, delete "an" and insert -- a -- , therefor.
Line 63, after "stripping" insert -- . --.

<u>Column 20,</u>
Line 15, delete "an" and insert -- a --, therefor.

<u>Column 21,</u>
Line 53, delete "taught" and insert in place thereof -- taut --.

<u>Column 29,</u>
Line 17, delete "292, 294" and insert in place thereof -- 272, 274 --.

UNITED STATES PATENT AND TRADEMARK OFFICE
CERTIFICATE OF CORRECTION

PATENT NO. : 6,665,483 B2
DATED : December 16, 2003
INVENTOR(S) : Gatica, Anthony W.

It is certified that error appears in the above-identified patent and that said Letters Patent is hereby corrected as shown below:

Column 34,
Line 49, delete "processes" and insert -- process --, therefor.

Column 35,
Line 13, delete the first occurrence of "appearance".
Line 28, after "invention" insert -- . --.

Column 36,
Line 42, delete "form" and insert -- from --, therefor.
Line 61, delete "A" and insert -- An --, therefor.

Column 37,
Line 11, delete "an" and insert -- a --, therefor.

Column 38,
Line 57, delete "02" and insert -- 20 -- therefor.

Signed and Sealed this

Twenty-second Day of June, 2004

JON W. DUDAS
*Acting Director of the United States Patent and Trademark Office*